United States Patent [19]

Horan et al.

[11] Patent Number: 5,665,328

[45] Date of Patent: Sep. 9, 1997

[54] COMPOUNDS, COMPOSITIONS AND METHODS FOR BINDING BIO-AFFECTING SUBSTANCES TO SURFACE MEMBRANES OF BIO-PARTICLES

[75] Inventors: Paul Karl Horan; Sue Ellen Slezak, both of Downingtown; Bruce D. Jensen, Schwenksville, all of Pa.

[73] Assignee: Phanos Technologies, Inc., Beverly Hills, Calif.

[21] Appl. No.: 984,269

[22] Filed: Dec. 1, 1992

Related U.S. Application Data

[63] Continuation of Ser. No. 189,192, May 2, 1988, abandoned.

[51] Int. Cl.$^6$ .................... A61K 5/00; C12Q 1/02
[52] U.S. Cl. .................... 424/1.17; 424/1.11; 435/29; 435/35
[58] Field of Search ............... 424/1.1, 9, 7.1; 534/10, 14; 436/544, 545, 546

[56] References Cited

U.S. PATENT DOCUMENTS

| | | |
|---|---|---|
| 925,429 | 10/1909 | Horan et al. . |
| 925,445 | 10/1909 | Horan et al. . |
| 3,228,904 | 1/1966 | Morris et al. . |
| 3,352,791 | 11/1967 | Sheehan et al. . |
| 3,673,410 | 6/1972 | Waite et al. .................... 435/35 |
| 3,706,566 | 12/1972 | Shiba et al. .................... 430/567 |
| 3,706,570 | 12/1972 | Nakazawa et al. .................... 430/567 |
| 3,916,069 | 10/1975 | Tiers et al. .................... 428/411 |
| 4,074,046 | 2/1978 | Mohan .................... 548/150 |
| 4,110,116 | 8/1978 | Beretta et al. . |
| 4,232,000 | 11/1980 | Fawzi .................... 424/1.1 |
| 4,232,121 | 11/1980 | Gilman, Jr. et al. .................... 435/32 |
| 4,343,782 | 8/1982 | Shapiro .................... 424/7.1 X |
| 4,352,751 | 10/1982 | Wieder et al. . |
| 4,400,370 | 8/1983 | Kass . |
| 4,419,511 | 12/1983 | Raue . |
| 4,424,201 | 1/1984 | Valinsky et al. .................... 424/7.1 X |
| 4,460,790 | 7/1984 | Reinehr et al. . |
| 4,473,652 | 9/1984 | Okazaki et al. .................... 436/536 |
| 4,500,509 | 2/1985 | Kass . |
| 4,555,396 | 11/1985 | Frank et al. .................... 435/34 |
| 4,582,700 | 4/1986 | Dean et al. .................... 424/1.1 |
| 4,652,519 | 3/1987 | Warshawsky et al. . |
| 4,670,545 | 6/1987 | Fritzeberg et al. . |
| 4,705,889 | 11/1987 | Hendricks et al. . |
| 4,714,606 | 12/1987 | Kass . |
| 4,748,129 | 5/1988 | Chang et al. .................... 436/519 |
| 4,762,701 | 8/1988 | Horan et al. .................... 424/1.1 |
| 4,775,625 | 10/1988 | Sieber . |
| 4,783,401 | 11/1988 | Horan et al. .................... 424/7.1 X |
| 4,859,584 | 8/1989 | Horan et al. .................... 424/9 X |
| 4,906,750 | 3/1990 | Gunther et al. . |
| 5,015,463 | 5/1991 | Dougherty et al. . |
| 5,093,106 | 3/1992 | Dzbanovsky et al. . |

FOREIGN PATENT DOCUMENTS

| | | |
|---|---|---|
| 86330/82 | 1/1983 | Australia . |
| 1251764 | 10/1967 | Denmark . |
| 0106339 | 10/1983 | European Pat. Off. . |
| 86103694.5 | 10/1986 | European Pat. Off. . |
| 1477402 | 4/1967 | France . |
| 723316 | 2/1955 | United Kingdom . |

OTHER PUBLICATIONS

Chem. Abstract, vol. 109, No. 10, Abstract 84552m Sakai et al. Electrically Conductive Thin Films (1986).
Eugene C. Butcher et al., Journal of Immunological Methods, 37 (1980), pp. 109–121.
Eugene C. Butcher et al., Journal of Immunological Methods, 37 (1980) pp. 97–108.
Paul E. Wanda et al., The Journal of Histochemistry and Cytochemistry, vol. 30, No. 12, pp. 1297–1300 (1982).
Marcia G. Honig et al., The Journal of Cell Biology, vol. 103, Jul. 1986, pp. 171–187.
D. Axelrod et al., *Biochemistry*, vol. 17(17) (1978), pp.3604–3609/
P. Sims et al., *Biochemistry*, vol. 13(16) (1974), pp. 3315–3330.
J. Schlessinger et al., *Science*, vol. 195 (1977), pp. 307–309.
R. Klausner et al., *Biochemistry*, vol. 19(26) (1980), pp. 6199–6203.
C. Montecucco et al., *Biochimica et Biophysica Acta*, vol. 552 (1979).
Struck, D., et al., *J. Biol. Chem.*, vol. 255, No. 11, pp. 5405–5410 (1980).

*Primary Examiner*—Shean C. Wu
*Attorney, Agent, or Firm*—Rothwell, Figg, Ernst & Kurz

[57] ABSTRACT

Compounds, compositions, their methods of preparation and use in binding bio-affecting substances to the surface membrane of bioparticles, such as enkaryotic cells, without producing appreciable detrimental effect on morphology or physiological function of cells.

13 Claims, 7 Drawing Sheets

COMPOUNDS, COMPOSITIONS AND METHODS FOR BINDING BIO-AFFECTING SUBSTANCES TO SURFACE MEMBRANES OF BIO-PARTICLES

This is a continuation of application Ser. No. 07/189,192, filed May 2, 1988 now abandoned.

BACKGROUND OF THE INVENTION

1. Field of the Invention

The present invention relates to compounds for binding bio-affecting substances, such as therapeutic and diagnostic agents, to the surface membrane of viable bio-particles, including eukaryotic prokaryotic cells and viruses, without producing appreciable detrimental effects on morphology or physiological function of the bio-particle to which the compounds are bound. The invention also relates to compositions and methods enabling binding of such compounds to bio-particles and to the use of the resultant particles for producing a site-specific predetermined effect, e.g., a diagnostic or therapeutic effect, in vivo.

2. Background Information

Numerous compounds and compositions are known which are capable of binding bio-affecting substances to carrier cells for various diagnostic applications. Fluorescent labeling techniques using a wide range of fluorochromes have been reported, such as cyanine derivatives, U.S. Pat. No. 4,343,782, fluorescein isothiocyanate, Butcher et al., *J. Immunol. Methods*, 37, 109–21 (1980) and Butcher et al., *J. Immunol. Methods*, 37, 97–108 (1980) and fluoroscein or rhodamine having a single, relatively long aliphatic hydrocarbon substituent, Wanda et al., *J. Histochem. Cytochem.*, 30, 1297–1300 (1982). There has also been reported a non-reproducible labeling technique using 3,3'-di-n-octodecyloxacarbocyanine for retrograde labeling of neurons Honig et al., *J. Cell Biology*, 103, 171–87 (1986). These prior art cell labelling compounds have been found to be: 1) unstable in the plasma membrane for long periods of time, and/or 2) cytotoxic or otherwise detrimental to cell function or morphology, and/or 3) not capable of providing reproducible results.

Diagnostic techniques utilizing chelate-metal ion complexes for radiographic and nuclear magnetic resonance imaging are fairly well developed. The use of complexes of Gallium-67, Indium-111, and Technetium-99 m in radio-imaging techniques have been widely reported. See, for example, Holman, ed., Radionuclide Imaging of the Brain (New York: Churchill Livingstone, 1985). The use of paramagnetic complexes in NMR imaging has been extensively investigated and compositions including such complexes have been proposed for administration as image enhancers. See, Australian Patent application 86 330/82 of Greis et al., filed Jul. 22, 1982. Insofar as is known, however, such imaging techniques do not result in membrane binding but rather the imaging complex is taken up into the cell and binds to the reticulum of the cell. In these applications, the chelating agent, e.g., oxine, tropolone or merc, have a toxic effect on many cells, such as lymphocytes, and are not optimal for imaging. Furthermore, since the detectable metal ion is taken into the cell, isotopic decay can more easily result in radiation damage to the cell's genetic material.

European Patent application Serial No. 86103694.5, published Oct. 22, 1986, describes a method for the selective irradiation of biological materials, particularly tissues, cells or cell components, in which the Mossbauer absorption frequency of a component of the material to be irradiated is determined and the material is then irradiated with gamma radiation of the corresponding Mossbauer absorption frequency with internal conversion and emission of gamma radiation and/or Auger electrons. The method is disclosed as being useful for selective radiation therapy providing selective tissue damage or necrosis, e.g., in cancer therapy, and for differentiating between diseased and healthy tissues. In practicing this method, Mossbauer isotopes are administered parenterally but are not selectively delivered to the tumor cells. It is believed that the selectivity in tumor cell kill will be achieved either through differences in absorption wavelengths of Mossbauer atoms within tumor cells and normal cells or by specifically focusing the absorbed radiation at the tumor itself.

One of the major goals of any pharmaceutical development is to provide drug therapy which is totally specific for a target cell type or disease site. In some cases, the compounds used are antagonists or agonists where specific receptors are found on cells to which therapy is directed and lower levels or affinities on other cell types. In other cases, the drug is specifically taken up by cells at the disease site or metabolized at the disease site in a way which is different from the matabolism at non-disease sites.

In treating cancer, many drug therapies proceed on the assumption that cancer cells are growing and metabolizing at a rate which is greater than most non-tumor cells. This assumption generally is flawed by the fact that hair follicles, bone marrow cells and gastro-intestinal cells grow at even faster rates and are often quite affected by these therapies. But even in cancer therapies, the goal is to try to deliver the therapy only to the tumor cells.

One recent attempt at this goal is to use monoclonal antibodies, as described in published European Patent application No. 83400461.6. With this therapy, the monoclonal antibody has "specific" binding affinity for the tumor cells. Radio-therapy or chemotherapeutic molecules are bound (covalent or ionic) to the monoclonal and injected intravenously into the patient. The monoclonal then migrates to the tumor site where it binds to the tumor cells with sufficiently high affinity to allow for the accumulation of radiation or chemical damage to be accrued by the tumor cells. This "therapy" is frought with a number of problems, not the least of which is the large amount of protein which must be injected for each treatment, making this therapy quite expensive. Additionally, the monoclonals injected are foreign protein and often results in the generation of antibodies by the patient against the therapeutic molecule. Furthermore, specificity of binding is often a problem and non specific toxicity is the result. Antigen shedding or modulation is equally problematic for this methodology, as well as limited capability to enter poorly vascularized tumors. In general, a methodology which could deliver a desired therapeutic effect specifically to tumor sites, is a desirable attribute for a pharmaceutical substance.

In copending U.S. patent application Ser. No. 925,192, filed Oct. 31, 1986 now U.S. Pat. No. 4,783,401, methods are disclosed for reproducibly labeling viable cells with symmetrical cyanine dyes that do not significantly affect cell viability. Applications for such labeled cells include using labeled red blood cells to distinguish post-transfusional bleeding from immunologic reaction and using dilution to measure growth rate of cultured cells.

In copending U.S. patent application Ser. No. 925,445, filed Oct. 31, 1986 now U.S. Pat. No. 4,762,701, methods are disclosed for tracking cells in vivo and for determining in vivo cell lifetimes. In performing such methods, cells are labeled with cyanine dyes and detection is by measuring fluorescence, absorbance, or by detecting nuclear magnetic reasonance probes included in the cyanine dyes. The methods are useful, for example, to measure red blood cell and platelet lifetimes, to track cells to determine sites of primary or metastatic tumors, or sites of occult infection, and to determine rates at which cells pass through vessels for assessing blood vessel patency and platelet aggregation.

In copending U.S. patent application Ser. No. 925,429, filed Oct. 31, 1986 now U.S. Pat. No. 4,859,584, methods are disclosed for determining growth rate of cells growing in vivo and in vitro. In carrying out such methods, cells are labeled with cyanine dyes and changes in plasma membrane cyanine dye levels are used to determine growth rate. The resulting cell growth rate determinations are utilized to monitor transplanted bone marrow cell engraftment and post-surgical corneal epithelial cell growth. Such methods also are useful for determining tumor cell sensitivity to cancer therapeutic agents, yeast sensitivity to antifungal agents, bacteria sensitivity to antifungal agents, and bacteria sensitivity to antibacterial agents.

SUMMARY OF INVENTION

It has now been discovered that bio-affecting compounds may be reproducibly bound to the surface membrane of cells, both eukaryotic and prokaryotic, and to viruses with sufficient affinity to prevent dissociation of the compound from the membrane and without adversely affecting the normal functioning of the cell or virus.

According to one aspect of the invention, compounds are provided having the capability of binding in the lipid phase of the surface membrane of cells or viruses. These compounds comprise a bio-affecting moiety, preferably a diagnostic or therapeutic agent, and at least one hydrocarbon substituent selected so that the compound is sufficiently non-polar as to have a surface membrane retention coefficient of at least 90 over 24 hours in saline containing 10 percent serum and further selected so that the compound solubility determination factor of the compound has no more than a 20% change over a two hour time period in the binding medium of choice. Suitable compounds are those of the formula $R-B-R_1$, wherein B represents the bio-affecting moiety and R and/or $R_1$ represent relatively long chain hydrocarbon substituents or "tails" that impart the requisite lipophilicity to the compounds. Once embeded in the membrane of a cell or virus the compounds do not appreciably adversely influence the normal function thereof, or have detrimental effect on viability of cells or viruses to which they are bound, which cells are sometimes referred to herein as carrier cells or viruses.

The number of linear carbons in the hydrocarbon tail(s) of the compounds of the invention is an important factor in achieving binding of the compounds of the invention to surface membranes of prokaryotic or eukaryotic cells or viruses. Experience with use of cyanine derivatives as diagnostic agents indicates that hydrocarbon tails of less than 3 carbons causes the cyanine to penetrate the plasma membrane and the nuclear membrane of cells resulting in staining of RNA and DNA. If carbon tails have a length greater than 3 carbons and less than 12 carbons, the compound no longer binds RNA and DNA but responds to membrane potential and enters the mitocondria (U.S. Pat. No. 4,343,782 to Shapiro and U.S. Pat. No. 4,424,201 to Valinsky, T. J. Lampidis et al., *Agents and Actions*, 14, 751–757, 1984). When the sum of the linear carbons in the hydrocarbon tail(s), is 23 or greater the lipophilicity of the molecule is increased such that it is retained in the plasma membrane and will not leak or transfer to other cells. In general, the longer the hydrocarbon tail, the higher the lipophilicity. Hydrocarbon tails having more than 30 linear carbon atoms, however, may pose a problem because the bio-affecting moiety and the reactant used to provide the hydrocarbon tail may not be soluble in the same solvent, making the chemistry of joining the hydrocarbon tail to the bio-affecting moiety quite difficult. Thus, there may be a practical limitation on the length of the hydrocarbon tail(s) depending on the chemical nature of the bio-affecting moiety to which it is to be bound.

According to another aspect of the invention, there is provided a composition for binding a bio-affecting moiety to a carrier cell or virus, which comprises a compound of the invention dissolved in a medium which is iso-osmotic for the cell or virus to which the compound is bound and which allows for consistent solubility of the compounds, with the dissolved compound being in a form that reproducibly binds to plasma membranes. The cell binding media which may be used in the practice of this invention include sugars, sugar-alcohols, amino acids, a Good's buffer, or a combination thereof, in which the compounds of the invention are stably soluble.

According to a further aspect of the invention, there is provided a method for preparing a carrier cell bearing a bio-affecting moiety capable of reproducibly exerting a site-specific predetermined effect, e.g., a diagnostic or therapeutic effect, in vivo. The desired effect may be exerted, for example, directly on a carrier cell, or on a cell group comprising such carrier cell. The preparative method essentially involves contacting a compound of the invention with the carrier cell or virus in the presence of a medium of the type described above, under conditions causing binding of the compound to the carrier cell or virus. The preparative method of the invention occurs without appreciably diminishing viability of the carrier cell or virus, or otherwise adversely affecting the desired physiological function thereof.

According to yet another aspect of the invention, there is provided a method for exerting a site-specific predetermined effect in vivo by exposure of the target site to a bio-affecting moiety capable of producing the desired effect. The method involves providing a carrier cell or virus to which is bound a compound of the invention, and delivering the bound carrier cell or virus to the site where the bio-affecting moiety is to produce its intended effect.

The present invention possesses a number of advantages as compared with the above-discussed prior art particularly with respect to applications involving cell binding. First, the compounds of the invention are bound to carrier cells in such a way as to place the bio-affecting substituent on the exterior of the cell. In many applications this provides a distinct advantage versus prior art techniques for binding bio-affecting substances to cells, in which the bio-affecting substance is caused to penetrate beyond the plasma membrane and into the cytoplasm or mitochondria. In radioisotope labeling, for example, placement of Indium or Technetium on the outside of the plasma membrane lowers the probability that emitted gamma radiation will pass through the nucleus of the cell, thus reducing the risk of undesired mutation or cell death. Such disruption of normal cell function is a serious problem with radiopharmaceuticals, such as the Indium-oxine or Indium-tropolone which are currently used. As a result of carrier toxicity and Indium toxicity upon the host cell such methods are considered sub-optimal for labeling of lymphocytes.

Furthermore, where toxic, chemotherapeutic, or radio-therapeutic agents are bound to the plasma membrane of a cell as the bio-affecting moiety in accordance with the invention, the carrier cell avoids the toxic or chemotherapeutic effects but travels to the target site where the intended toxic or chemotherapeutic effect of the bio-affecting moiety is exerted on surrounding cells.

In other applications, monoclonal antibodies, lectins, agonists or antagonists to tissue receptors, glycosaminoglycans, sialic acids or other such molecules may be placed on the exterior surface of the cell to alter the migration patterns of the cell. While some biomolecules such as glycosaminoglycans and sialic acids may affect specific migration routes, others like monoclonal antibodies, agonists or antagonists to tissue receptors, or lectins may effect the retention time of a cell at a specific site.

A further notable advantage is that binding of the compounds of the invention to carrier cells occurs in the lipids. This is significant because binding in lipids reduces the chance of interfering with the important functional domains of a cell membrane which lie in the discrete protein portions and not in the more extensive lipid regions. Those prior art procedures for delivering bio-affecting substances to cells which involve binding to proteins and cell receptors often result in diminished functional capacity, as noted above.

There are certain concomitant benefits realized from binding in the lipid regions of cells. Since the lipid regions comprise the vast majority of the surface area of the cell, it is possible to place larger numbers of lipid binding compounds into the plasma membrane. Moreover, because the compounds of the invention are incorporated into membrane lipids, they are generally insoluble in normal physiological salts. Accordingly, once the compounds are bound to the membrane, they are effectively trapped there and cannot dissociate easily. Consequently, the compounds do not leak from the cells, and when a labeled cell encounters another cell or membrane, the compound is not transferred from cell to cell.

Binding in the membrane lipids is also advantageous in that the bound compounds are generally non-immunogenic. The immune system does not respond as readily to changes in the lipid regions of the cell membrane as to changes in the protein portion. Thus, with a sufficiently small bio-affecting moiety, the compounds of the invention would not be expected to generate a humoral or cellular immune response against them. If, on the other hand, a cellular or humoral response is desired, it is possible to use bio-affecting moieties of sufficient size and immunogenicity to elicit the desired response, which might be beneficial, for example, in vaccine production.

Knowledge of the migration patterns of immune and hematopoeitic cells to specific disease sites is also used to advantage in the practice of this invention. With such information, compounds of this invention may be administered to target therapeutic molecules to the site of disease and only minimally affect non-disease sites.

Using cell targeting therapies, the therapeutic-agent will not enter the liver cells, unless the cell to which it is bound is dead. In this way, the optimal therapeutic effect will be exerted on the specific site to which the bound cell migrates, as metabolism of the therapeutic agent in the liver will be avoided.

BRIEF DESCRIPTION OF THE DRAWINGS

Referring to the drawings herein.

DETAILED DESCRIPTION OF INVENTION

Figure 1A:
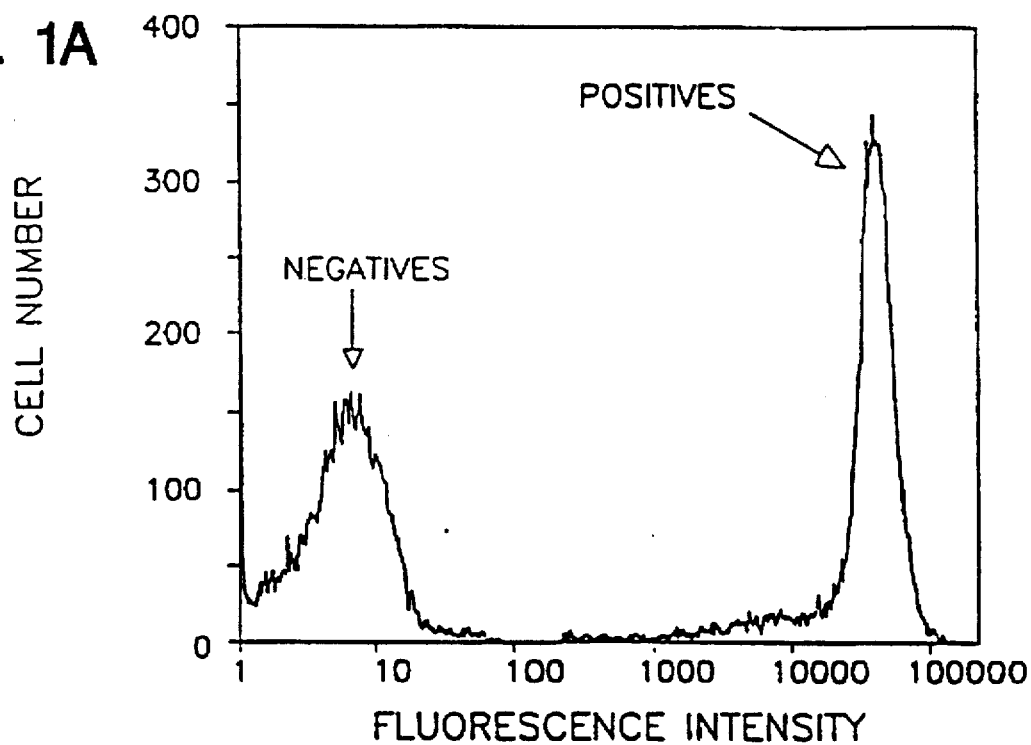
FIG. 1 graphically represents fluorescence intensity distribution measurements for Yac-1 cells labeled with DiO-C14-(3), with FIG. 1A showing the intensity difference of stained versus non-stained cells.
FIG. 1B showing a decrease in fluorescence intensity as a function of time.

The expression "viable bioparticle capable of physiological function" is used herein to refer to any viable cell or membrane-containing virus. Moreover, as used herein, the term "cell" includes prokaryotic cells, such as bacteria, as well as nucleated eukaryotic cells, such as white blood cells, various tumor cells, and mammalian cells in culture, e.g., chinese hamster ovary cells, yeast, and non-nucleated cells, such as red blood cells, red blood cell ghosts and platelets. The detailed description of the invention hereinbelow is set forth with particular reference to cells. It should be understood, however, that what is stated with respect to cells is generally applicable to membrane-containing viruses, as well.

The terms bio-affecting substance and bio-affecting moiety are used interchangeably herein to refer to a wide variety of different substances useful in the therapeutic, diagnostic, prophylactic or other treatment of humans or animals. The substances useful in therapeutic applications of the invention include those capable of preventing, alleviating, treating or curing abnormal or pathological conditions of the living body. The diagnostic applications of the compounds include, for example, determination or detection of a physiological condition or state by an in vivo or in vitro test. The bio-affecting substances useful in the practice of this invention further include those capable of maintaining, increasing, decreasing, limiting or destroying a physiologic body function, as well as substances for protecting a living body by inhibiting, killing, modifying or retaining a microorganism or antigen thereof. Derivatives of such substances having long hydrocarbon tails, as described in further detail below, may be beneficially used in any of these general categories of application. Particularly preferred are bio-affecting moieties which function as diagnostic or therapeutic agents.

In the case of diagnostic applications, the compounds of the invention effectively serve as reporter molecules which may be detectable from outside the body, or may require removal of a body fluid or biopsy for analysis in vitro, the former procedure, allowing for non-surgical assessment of a physiological condition, may be preferred.

When used in therapeutic applications, a compound of the invention is bound to a selected cell type and introduced into the body with the result that the desired therapy is directed against the abnormal or pathological condition, or the normal migration or circulation pattern of the carrier cell is altered, so that the therapeutic agent is delivered, as desired.

In any case, the compounds of the invention exhibit no appreciable cytotoxic effect on the carrier cell, nor otherwise produce any appreciable detrimental effect on desired cell function.

The diagnostic agents comprising the compounds of the invention may be selected from diverse classes of substances that are detectable by various analytical procedures known to those skilled in the art. One such class of substances suitable for diagnostic application includes those in which the bio-affecting moiety is a fluorescent compound. A composition comprising such a compound in a solvent of the type described herein may be readily applied to carrier cells so that the compound is bound to the plasma membrane of the cells. The cells are then rendered fluorescent, and are thus detectable ex vivo, thereby providing some indication about in vivo activity of the cell. Such fluorescent compounds are preferably cyanine dyes and their derivatives, including, e.g., oxacarbocyanine, indocarbocyanine, thiocarbocyanine, or acridine dyes and derivatives thereof. Other useful fluorescent compounds include, for example, styrlpyridine, anthraquinone, coumarin, xanthene, phenoxazine, phenothiazine, or diphenylhexatriene dyes and derivatives thereof. The fluorescent moieities preferably have a positive charge which helps in incorporation and retention in the plasma membrane.

Other useful diagnostic agents are chelating substances complexed with metals, which may be directly or indirectly detectable. Thus, the chelate-metal complex may comprise an isotope selected from the transition metal series whose atomic number is from 21–49, such as Indium-111 or Technetium-99 m. Such complexes may be bound to the cell plasma membrane rendering it radioactive, so as to permit imaging using a gamma camera after injection of the labeled cells into the body. Chelating substances may also be complexed with an ionic species of metal which is indirectly detectable, e.g., by reason of certain effects produced thereby at the site of interest. Complexes of paramagnetic elements, for example, are capable of influencing the relaxation times of nearby nuclei, which is detectable by magnetic resonance imaging (MRI). Chelate-metal complexes comprising a metal ion selected from the transition metal series whose atomic number is from 21–29, the lanthanide series whose atomic number is 59–66 and the actinide series whose atomic number is 91, may be suitable for such purpose.

Compounds comprising radioisotopic atoms may also be used, if desired, in diagnostic applications of this invention. A radioisotope such as $^{125}I$, $^{131}I$, $^{14}C$, $^{3}H$, $^{32}P$, $^{35}S$, $^{75}Se$ may be substituted for the more abundant but non-radioactive form of the naturally occuring atom present in the bio-affecting moiety or the hydrocarbon tail portion of the compound. A suitable formulation of such compound applied to carrier cells (or viruses), so that the compound is bound to the plasma membrane of the cells (or membrane of the virus), renders the cells (or viruses) radioactive and permits imaging using conventional radiographic detection equipment, such as a gamma camera or standard beta counting procedures. Isotopes having non-zero spin states may also be introduced into the compounds of the invention, so as to make their presence detectable using MRI techniques.

For therapeutic applications, the bio-affecting moiety may be a chelating agent of the type described above, complexed with an alpha-emitting radionuclide, or a moderate energy beta emitting isotope, such as $^{67}Cu$. A composition of such a complex in an appropriate solvent is bound to carrier cells and washed carrier cells are injected into the patient for delivery to the disease site to provide local radiation sufficient to interrupt the disease process.

As another form of the therapeutic bio-affecting moiety, a chelating agent may be complexed with a Mossbauer isotope. A formulation of said complex could be applied to cells for injection into the patient, where they would track to the disease site. Thereafter, a low level of whole or partial body radiation of appropriate wave length would be applied so that the Mossbauer atom could absorb the applied radiation, emiting Auger electrons in a manner analogous to the procedure described in European Patent Application Number 86103694.5, supra, which provides numerous examples of Mossbauer isotopes useful for this purpose. In this particular application, however, since the carrier cells would deliver the Mossbauer isotope to the disease site, the radiation could be administered without having to determine the location of the disease site in advance.

Proteinaceous substances, including proteins, glycoproteins, lipo-proteins or peptides may also be coupled to hydrocarbon tails of appropriate length for the therapeutic applications in accordance with the present invention. Representative bio-affecting proteinaceous substances are toxins, hormones, enzymes, antigens, antibodies and antibody fragments. An appropriate formulation of such compound would be applied to cells for injection into a patient. For example, tPA may be bound to the surface of a red cell, which, when delivered to a fibrin clot, dissolves the fibrin to permit reperfusion. The tPA would be expected to have no appreciable effect on the carrier cell to which it is bound. Similarly, antibody molecules may be bound to the surface of a monocyte and, while having no effect on the monocyte, may bind to a tumor cell and direct the monocyte to kill the tumor cell.

In another therapeutic application of the compounds of the invention, the bio-affecting moiety is a carbohydrate capable of altering the migration and circulation patterns within the body of cells to which it is bound. One class of carbohydrates applicable in this way includes sialic acids; another includes the glycosaminoglycans. For example, a formulation comprising a sialic acid could be applied to the plasma membrane of red cells to increase the number of sialic acids on the membrane. The increase in the number of charge groups should increase the lifetime of the red cells in circulation before removal in the liver.

The bio-affecting moiety may also be in the form of a ligand capable of binding to receptors on cells within target organs. Compounds containing such ligands, when bound to cells, would enable the migration of cells to be directed to specific organ sites.

The bio-affecting moieties are used in the form of derivatives which enable binding to the plasma membrane of carrier cells. These derivatives are compounds of the formula R-B-$R_1$ wherein B represents a bio-affecting moiety and R and $R_1$ represent substituents independently selected from the group of hydrogen, alkyl, alkenyl, alkynyl, alkaryl or aralkyl, the hydrocarbon chains of which are linear or branched, the substituents being unsubstituted or substituted with one or more non-polar functional groups, one of R or $R_1$ having at least 12 linear carbon atoms and the sum of the linear carbon atoms in R and $R_1$ totalling at least 23, and provided that when B represents cyanine, R is different from $R_1$. The R and/or $R_1$ groups are so selected that the plasma membrane retention coefficient of the compound (as described below) is at least 90 over 24 hours in saline containing 10% serum, and that the compound solubility determination factor of the compound has no more than a 20% change over a two hour time period in the binding medium of choice. As used herein, the expression "non-polar functional group" refers to substituents such as O-alkyl, S-alkyl, halogen, N(alkyl)$_2$, Se-alkyl, NO, CN, CO-alkyl, C=N-alkyl, —SiMe$_3$, O—SiMe$_3$, and the like.

A preferred class of fluorescent compounds within the scope of the invention are cyanine derivatives of the formula

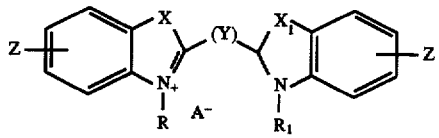

wherein R and R$_1$ are different and represent substituents independently selected from the group of hydrogen, alkyl, alkenyl, alkynly, alkaryl or aralkyl, the hydrocarbon chains of which having from 1 to 30 carbon atoms, and being linear or branched, said substituents being unsubstituted or substituted with one or more non-polar functional groups, one of R or R$_1$ having at least 12 linear carbon atoms, and the sum of the linear carbon atoms in R and R$_1$ being at least 23;

X and X$_1$ may be the same or different and represent O, S, C(CH$_3$)$_2$ or Se;

Y represents a linking group selected from —CH=, —CH=CH—CH=, —CH=CH—CH=CH—CH=, or —CH=CH—CH=CH—CH=CH—CH=;

Z represents a substituent selected from the group H, alkyl, OH, NH$_2$, COOH, CONH$_2$, SO$_3$H, SO$_2$NH$_2$, CONH-alkyl, CON-(alkyl)$_2$, NH-acyl, —O-alkyl, NH-alkyl, or N(alkyl)$_2$, SH, S-alkyl, NO$_2$ or halogen, the alkyl groups comprising said Z substituents having from 1 to 3 carbon atoms;

and A represents a biologically compatible anion.

Particularly good results in the practice of this invention are achievable using cyanine derivatives of the formula

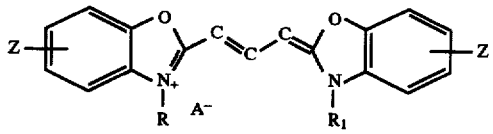

wherein R and R$_1$ are different and represent alkyl substituents, having from 1 to 30 carbon atoms, and being linear or branched, unsubstituted or substituted with halogen, one of R or R$_1$ having at least 12 linear carbon atoms and the sum of the linear atoms in R and R$_1$ being at least 23;

Z represents a substituent selected from the group H, or lower alkyl having from 1 to 3 carbon atoms; and A represents a biologically compatible anion.

Another preferred class of fluorescent compounds within the scope of the invention are acridine derivatives of the formula

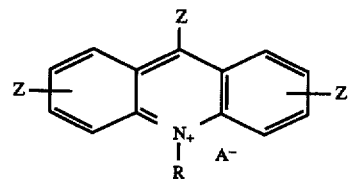

wherein R represents a substituent selected from the group of alkyl, alkenyl, alkynyl, alkaryl or aralkyl, the hydrocarbon chain of which is linear or branched, said substituent being unsubstituted or substituted with one or more non-polar functional groups, and having at least 23 linear carbon atoms;

Z represents a substituent selected from the group H, alkyl, OH, NH$_2$, COOH, CONH$_2$, SO$_3$H, SO$_2$NH$_2$, CONH-alkyl, CON(alkyl)$_2$, NH-acyl, —O-alkyl, NH-alkyl, or N(alkyl)$_2$, SH, S-alkyl, NO$_2$, halogen, the alkyl groups comprising said Z substituents having from 1 to 3 carbon atoms; and A represents a biologically compatible anion.

A further preferred class of compounds within the scope of the invention are chelating agents of the formula A chelating agent having the formula:

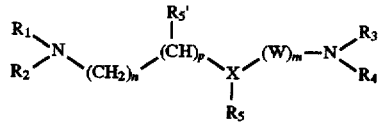

n being a number from 0 to 2; m being a number from 0 to 2; and p being either 0 or 1, wherein R$_1$, R$_2$, R$_3$ and R$_4$ independently represent substituents selected from the group of:

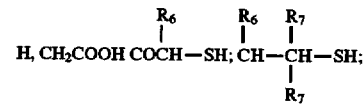

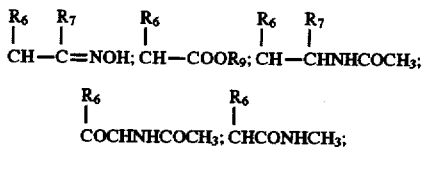

C$_1$–C$_{30}$ alkyl, C$_1$–C$_{30}$ alkenyl, C$_1$–C$_{30}$ alkynyl, and unsubstituted or substituted aryl aralkyl, said last-mentioned substituents being selected from hydroxyl, halogen, thiol, C$_1$–C$_{30}$ alkyl, C$_1$–C$_{30}$ alkenyl, C$_1$–C$_{30}$ alkynyl or aryl or aralkyl; O-(C$_1$–C$_{30}$ alkyl, alkenyl or alkynyl); S-(C$_1$–C$_{30}$ alkyl, alkenyl or alkynyl); NH(C$_1$–C$_{30}$ alkyl, alkenyl or alkynyl); N$^+$R$_{11}$ (C$_1$–C$_{30}$ alkyl, alkenyl or alkynyl)$_2$; N(C$_1$–C$_{30}$ alkyl, alkenyl or alkynyl)$_2$ W represents CH$_2$ or C=O;

X represents CH or N;

R$_5$ and R$_5'$ independently represent H, CH$_2$CO$_2$H, or Y-R$_8$;

Y represents the linking group O, C=O, S, (CH$_2$)$_x$ or Se, x being a number from 0 to 5;

R$_6$ and R$_7$ independently represent H or C$_1$ to C$_2$ alkyl;

R$_8$ represents a substituent selected from the group of —NH(C$_1$–C$_{30}$ alkyl, alkenyl, or alkynyl), N(C$_1$–C$_{30}$ alkyl, alkenyl or alkynyl)$_2$, N$^+$R$_{11}$(C$_1$–C$_{30}$ alkyl, alkenyl or alkynyl)$_2$, C$_1$–C$_{30}$ alkyl, C$_1$–C$_{30}$ alkenyl, C$_1$–C$_{30}$ alkynyl, unsubstituted or substituted aryl or aralkyl, said last-mentioned substituents being selected from the group of H, alkyl to C$_{30}$, alkenyl to C$_{30}$, alkynyl to C$_{30}$, alkaryl, aralkyl, —O-alkyl to C$_{30}$, —O-alkenyl to C$_{30}$, O-alkynyl to C$_{30}$, —O-aralkyl, —NR$_9$-alkyl to C$_{30}$, —NR$_9$-alkynyl to C$_{30}$, —NR$_9$-alkenyl to C$_{30}$, —NR$_9$-aralkyl, S-alkyl to C$_{30}$, —S-alkenyl to C$_{30}$, S-alkynyl to C$_{30}$, —S-aralkyl, N+R9R$_{11}$-alkyll to C$_{30}$, N$^+$R$_9$R$_{11}$- alkenyl to C$_{30}$, N$^+$R$_9$R$_{11}$-alkynyl to C$_{30}$, —NHCOR$_9$,

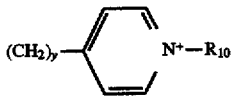

y being a number from 0 to 5;

R$_9$ represents a substituent selected from the group of H, C$_1$–C$_{30}$ alkyl, C$_1$–C$_{30}$ alkenyl, C$_1$–C$_{30}$ alkynyl or aralkyl;

R$_{10}$ represents a substituent selected from the group of C$_1$–C$_{30}$ alkyl, C$_1$–C$_{30}$ alkenyl, C$_1$–C$_{30}$ alkynyl, alkaryl or aralkyl;

R$_{11}$ represents a substituent selected from the group of H or C$_1$ to C$_3$ alkyl; and wherein at least one of the substituents R$_1$, R$_2$, R$_3$, R$_4$, R$_8$, R$_9$ or R$_{10}$ has a minimum of 23 carbon atoms, or the sum of the linear carbon atoms in any two of said substituents totals at least 23 carbon atoms.

Particularly preferred are chelating agents of the following formulae:

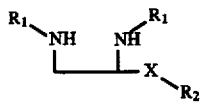

wherein R$_1$ represents COCH$_2$SH, CH(CH$_3$)C(CH$_3$) =NOH or CH$_2$C(Me)$_2$ SH;

X represents a carbonyl or methylene; and

R$_2$ represents a substituent selected from the group of NHR$_3$, NR$_3$R$_4$ or $^+$NR$_3$R$_4$R$_5$;

R$_3$ and R$_4$ represent substituents independently selected from the group of C$_1$–C$_{30}$ alkyl, C$_1$–C$_{30}$ alkenyl, C$_1$–C$_{30}$ alkynyl, aralkyl or alkaryl;

R$_5$ represents H or C$_1$ to C$_2$ alkyl; and at least one of the substituents R$_3$ or R$_4$ has a minimum of 23 linear carbons, or the sum of linear carbon atoms in R$_3$ and R$_4$ totals at least 23 carbon atoms.

Also useful are chelating substance of the formula:

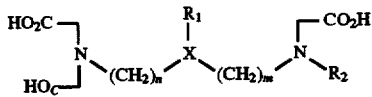

wherein n is 0 or 2; m is 1 or 2; X represents CH or N; one of R$_1$ or R$_2$ is CH$_2$CO$_2$H and the other of R$_1$ or R$_2$ represents a substituent selected from the group of alkyl, alkenyl, alkynyl, aralky or alkaryl, or CH$_2$–C$_6$H$_4$—NHCO-(alkyl, alkenyl, alkynyl, aralkyl, alkaryl), the hydrocarbon chain of which is linear or branched and contains at least 23 linear carbon atoms.

Chelating agents of this formula are preferably complexed with Indium. Of course, various other lipophilic chelating derivatives may be used in the practice of this invention, if desired.

A number of different synthetic routes may be used in preparing derivatives of bio-affecting substances having the formula R-B-R$_1$, as described above. These include:

(a) by an alkylation reaction between "B" or precursor to "B" and the hydrocarbon chain moiety R and/or R', involving nucleophilic displacement of a good leaving group, followed by elaboration of "precursor to B" if required. For example, O-alkylation by procedures analogous to those described by F. Fages et al., Bull. Soc. Chim. Fr., 959, 1985 or by Felgner et al., Proc. Nat. Acad. Sci., 84, 7413, 1987; N-alkylation by procedures adapted from A. Yamagishi, J. Phys. Chem., 85, 281, 1981; J. Sondermann, Liebigs Ann. Chem., 749, 183–197, 1971; or S. M. Karesh, Ph.D. Dissertation, University of Maryland, 1975; S-alkylation by procedures adapted from R. A. Pascal, Jr. and D. L. Ziering, J. Lipid Res., 27, 221, 1986 or L. H. DeRiemer et al., J. Labelled Cmpds and Radiopharm., 18, 1517, 1981.

(b) by an acylation reaction between "B" or "precursor to B" and the hydrocarbon chain moiety R and/or R', followed by elaboration of "precursor to B", if required. For example, O-acylation to form an ester linkage by procedures adapted from C. L. Penney et al., J. Org. Chem., 50, 1457, 1985 or A. W. Nicholas et al., Lipids, 18, 434, 1983; N-acylation to form an amide linkage by procedures adapted from T. G. Wensel and C. F. Meares in "Radioimmunoimaging and Radioimmunotherapy"; Burchiel, S., Rhodes, B. A., Eds.; Elsevier, N.Y., 1983, p. 1985 or S. Hirano and W. Ohashi, Carbo. Res. 59, 285–288, 1977.

(c) by an addition reaction between "B" or "precursor to B" and the hydrocarbon chain moiety R and/or R', involving an amino or hydroxyl function and an isocyanate or isothiocyanate functionality, followed by elaboration of "precursor to B" if required. For addition reactions to isocyanates, see Satchell and Satchell, Chem. Soc. Rev., 4, 231–250, 1975, and for addition reactions to isothiocyanates, see Walter and Bode, Angew. Chem. Int. Ed. Engl., 6, 281–293, 1967.

(d) by a condensation reaction between "B" or "precursor to B" and the hydrocarbon chain moiety R and/or R', involving an amino function and an aldehyde functionality to give a Schiff base derivative, followed by elaboration of "precursor to B" moiety, if required. For example, see European Patent No. 0088695 A2 and references cited therein.

Other suitable reaction schemes, including variations or modifications of those just mentioned, will occur to those skilled in the art.

Reaction schemes appropriate for the preparation of specific classes of compounds useful in the practice of this invention are as follows:

1. Fluorescent Compounds with Lipophilic Tails

Oxacarbocyanine derivatives may be prepared as shown in scheme 1 below. 2-Methylbenzoxazole (commercially available) is alkylated with an alkyliodide (RI) as described by J. Sims et al., Biochemistry, 13, 3315–3330, 1974 to give (1) which is reacted further with N,N'-diphenylformamidine (commercially available), by a method analogous to that described in U.S. Pat. No. 2,647,054, to give (2). Compounds (3) and (4) are prepared by the method of J. Sondermann, Liebigs Ann. Chem., 749, 183–197, 1971.

Alcohol (ROH) is treated with 4-chlorobenzenesulphonyl chloride (commercially available) to give (3) which is then reacted with 2-methylbenzoxazole to give (4). Intermediates (2) and (4) may be coupled together by refluxing in ethanol containing triethylamine (two equivalents) to yield oxacarbocyanine (5) (a modification of the procedure described in U.S. Pat. No. 2,647,054).

Acridine derivatives are prepared as shown in scheme 2 by a procedure analogous to the one described by A. Yamagishi et al., *J. Phys. Chem.*, 85, 281, 1981. 4-Chlorobenzenesulphonate (6) is prepared by the procedure of J. Sondermann, *Liebigs Ann. Chem.*, 749, 183–197, 1971, (see above), heated with acridine orange (7) (commercially available) and then treated with potassium iodide to yield acridinium iodide (8).

Suitable rhodamine B derivatives may be prepared as described by P. M. Keller et al., *J. Cell. Sci.*, 28, 167–177, 1977. This procedure is illustrated in scheme 3 and involves esterification of rhodamine B (9) (commercially available) with a lipophilic alcohol (ROH), via its acid chloride.

2. Metal Chelators with Lipophilic Tails

Scheme 4 illustrates two methods (a) and (b) for preparing aminopolycarboxylic acid-type chelators, e.g., ethylenediamine tetraacetic acid (EDTA), with lipophilic tails (R) which should be capable of complexing a wide range of metal cations.

Compound (12) may be synthesized by a procedure analogous to that described by W. C. Eckelman et al., *J. Pharm. Sci.* 64, 704, 1975. This procedure involves alkylation of diethylenetriamine (10) (commercially available) with an alkylbromide (RBr), followed by treatment with HBr to give (11). Intermediate (11) is then reacted with sodium chloroacetate to yield (12).

Another procedure involves synthesizing compound (13) from p-nitrophenylalanine (commercially available) as described by L. H. DeRiemer et al., *J. of Labelled Compds. and Radiopharm.*, 18, 1517–1534, 1981, and coupling (13) with an acid chloride (RCOCl), as described by T. G. Wensel and C. F. Meares in "Radioimmunoimaging and Radioimmunotherapy," Burchiel, S., Rhodes, B. A., Eds.: Elsevier, N.Y., 1983, p. 185, to give product (14).

The synthesis of three chelators suitable for complexing with Technetium are illustrated in scheme 5. These may be derived from intermediate (15) which has been prepared from ethyl 2,3-diaminopropionate (See E. F. Godefoi, *Chem. Abstr.*, 51:463; 1956) by S. M. N. Efange et al., *J. Nuc. Med.*, 28, 1012–1019, 1987. Reaction of (15) with a lipophilic amine RR'NH would furnish (16) which upon acidic hydrolysis would then yield (17). Compound (17) may be converted to chelator (18) by a method analogous to that of S. M. N. Efange et al. (*J. Nuc. Med.*, 28, 1012–1019, 1987) which involves treatment of (17) with 2,2'-dithio-bis(2-methylpropanal) (See H. F. Kung et al., *J. Nuc. Med.*, 25; 326–332, 1984) followed by the simultaneous reduction of the disulphide, the diimine and the amide with lithium aluminum hydride.

Alternatively, (17) may be converted to chelator (19) by a method analogous to that of R. O. Neiurinckx et al., *J. Nuc. Med.*, 28, 191–202, 1987, which involves treatment of (17) with 2,3-butanedione monoxime (commercially available) followed by reduction of the diimine with sodium borohydride.

As another alternative, (17) may be converted to chelator (20) by a procedure analogous to that described in U.S. Pat. No. 4,444,690, which involves reaction of (17) with chloroacetyl chloride followed by reaction with sodium thiobenzoate, after which cleavage of the benzoyl groups is effected with alkali.

3. Proteinaceous Substances with Lipophilic Tails

Four possible ways of attaching lipophilic tails to proteinaceous substances are described below.

(i) Via Cyanuric Chloride (trichlorotriazine)

This method is illustrated in scheme 6 and is analogous to the procedures described by C. W. Mahorey and A. Azzi, *Biochem. J.*, 243, 569–574, 1987, and D. Blakeslee and M. G. Baines, *J. Immuno. Meth.*, 13, 305–320, 1976. The lipophilic tail (R) is attached to cyanuric acid (commercially available) via nucleophilic displacement of one chlorine on cyanuric acid (21) by an alkyl amine, to give dichlorotriazinylaminoalkyl (22), this is then coupled to the protein to give (23) via another nucleophilic displacement of chlorine by an amino group on the protein.

(ii) Via Activated Esters

This method is illustrated in scheme 7 and is analogous to the procedure described by A. Huang et al., *Biochimica et Biophysica Acta*, 716, 140–150, 1982. The activated ester (24) of an acid with a lipophilic tail, R, is formed and undergoes a nucleophilic displacement reaction at the ester carbonyl with the amino group of a protein. The activated ester may be N-hydroxysuccinimide, trichlorophenol or p-nitrophenol and is usually formed by coupling of the acid and alcohol with dicyclohexylcarbodiimide.

(iii) Via Addition to Isothiocyanate

This method is illustrated in scheme 8 and is analogous to the procedures described by Esteban et al., *J. Nuc. Med.*, 28, 861, 1987 and C. F. Meares et al., Anal. Biochem. 142, 68–78, 1984. The lypophilic tail, R, is attached to the protein by the addition reaction of an amino residue on the protein to an isothiocyanate functionality on the lipophilic moiety forming a thiourea linkage.

(iv) Via Schiff Base Formation

In the case of glycoproteins, the carbohydrate side chain may be selectively oxidized by chemical or enzymatic means and the resulting aldehyde functionality reacted with a lipophilic amine to form a Schiff base derivative. The Schiff base derivative could then be reduced with sodium borohydride or sodium cyanoborohydride to form a more stable adduct if required. This procedure would be analogous to the one described in European Patent 0088695 A2.

4. Carbohydrates with Lipophilic Tails

Syntheses of N-acetyl-D-neuraminic acid derivatives with lipophilic tails may be prepared by a procedure analogous to that described by H. Ogura et al., *Carbo. Res.*, 158, 37–51, 1986, as shown in scheme 9.

Compound (26), prepared by H. Ogura et al. from N-acetyl- -D-neuraminic acid (25) (from edible bird nest) by reaction with acidic methanol and then acetyl chloride, may undergo a Koenigs-Knorr reaction with a lipophilic alcohol, ROH, to give (27) as a mixture of $\alpha$ and $\beta$ anomers, which upon treatment with sodium hydroxide to cleave the methylester and O-acetates should furnish lipophilic derivatives (28).

Suitable hexarin derivates may be prepared using a procedure analogous to that described by S. Hirano and W. Ohashi, *Carbo. Res.*, 59, 285–288, 1977, which involves reacting N-desulphated heparin with a lipophilic anhydride to give an N-acyl derivative.

SCHEME 1
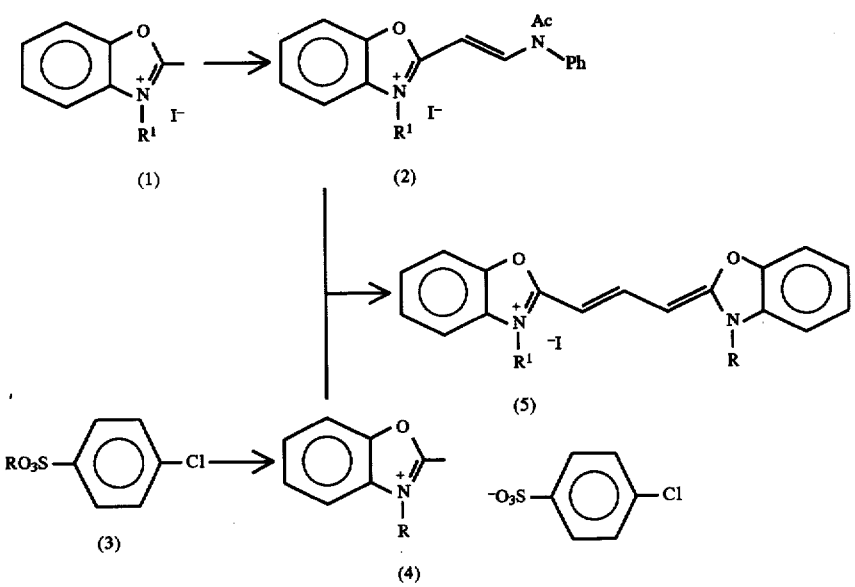
SCHEME 2
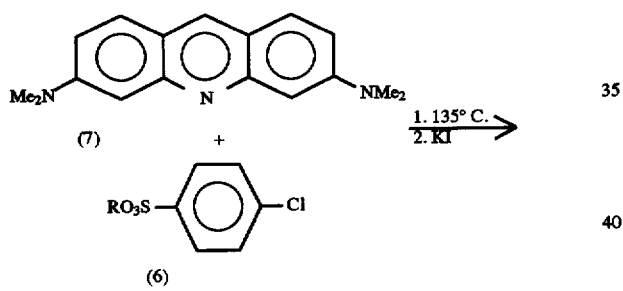
SCHEME 3
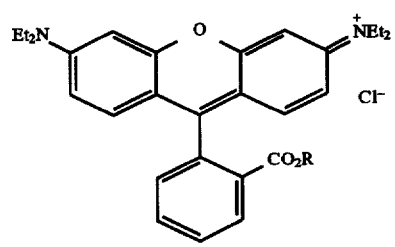
-continued
SCHEME 3
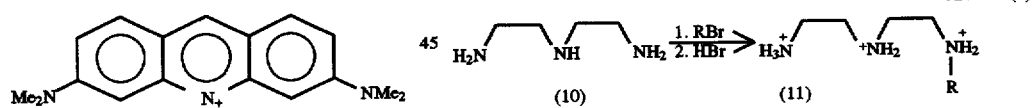
SCHEME 4
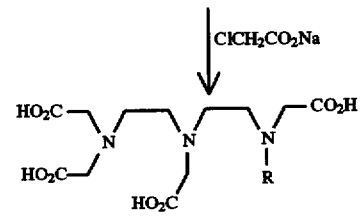
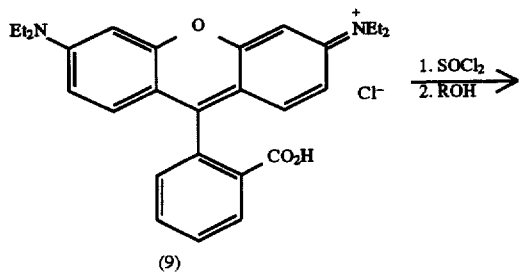
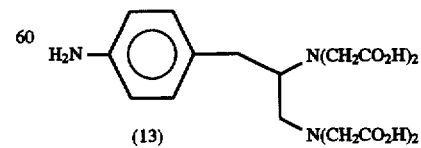

5,665,328
SCHEME 4
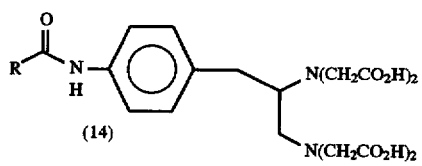
SCHEME 5
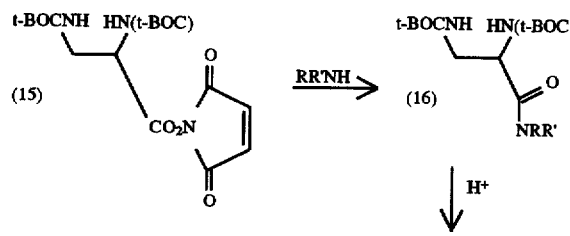
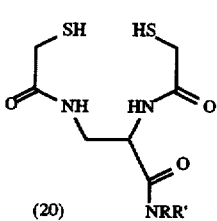
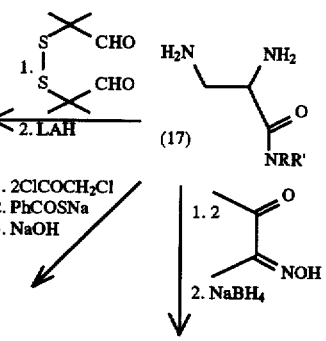
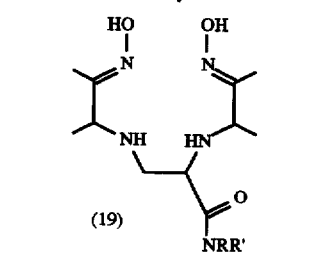
SCHEME 6
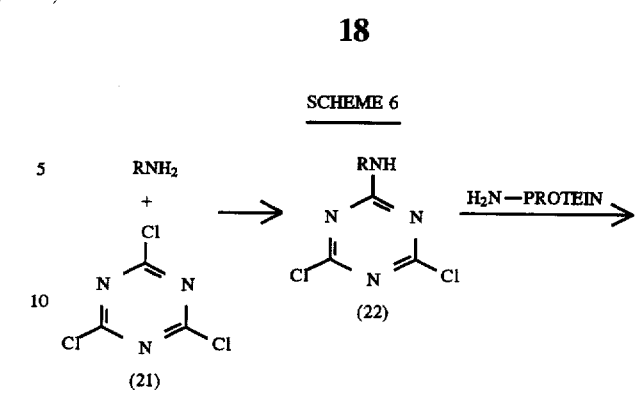
SCHEME 7
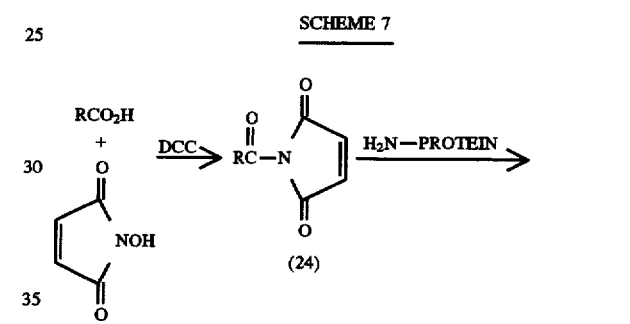
SCHEME 8
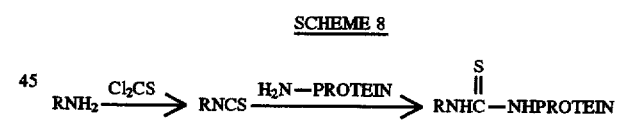
SCHEME 9
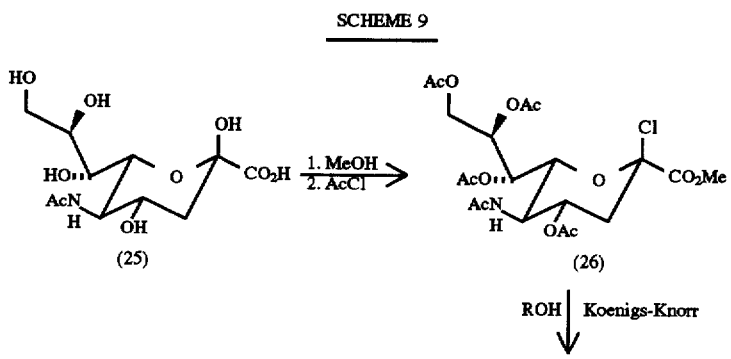

-continued
SCHEME 9

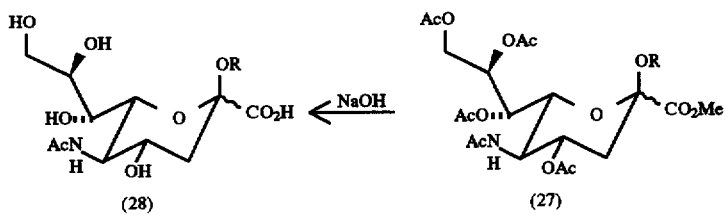

(28)     (27)

As previously noted, the nature of the hydrocarbon tails substituted on the compounds of the invention are important to the success of binding the bio-affecting moiety to the plasma membrane of the cell. In compounds having a single hydrocarbon tail, e.g., acridine derivatives, the linear number of carbons should be 23 or greater. In compounds having two or more hydrocarbon tails, one of the tails must have a linear length of at least 12 carbons, with the sum of the linear carbon atoms in the hydrocarbon tails being at least 23. The membrane retention coefficient should be at least 90. In other words, at least 90% of the compound being tested must be retained over a 24 hour period. The procedure for determining the membrane retention coefficient is exemplified hereinbelow.

As previously mentioned, the compounds of the invention must be capable of binding to the carrier cells without appeciable toxocity to the carrier cells. To determine the extent of cytotoxicity, cells are exposed to a compound of the invention at a variety of concentrations, including zero concentration. The cells are then exposed to trypan blue or propidium iodide (Celada, F. and Rotman, B., Proc. Natl. Acad. Sci., 57, 630, 1967). These dyes are normally excluded by a living cell and only permeate the membrane of a dead cell. After the appropriate incubation time the cells are examined with a microscope or a flow cytometer and the percentage of stained cells (percent dead) is determined. A compound is acceptable for the applications described herein, only if the cytotoxicity is less than 10% at the concentrations of compound used for cell binding. All the compounds specifically exemplified hereinbelow satisfy this criterion.

Binding of the compounds of the invention to carrier cells should also exert no appreciable detrimental effect on desired cell functions. Since the practice of this invention utilizes cells as carrier vehicles, it is important that binding of the compounds of the invention to cells, does not alter cell functions which are important to their ability to perform as carriers. For example, it may be important for the labeled cell to divide in order for it to perform in a given application. On the other hand, the compound used may alter some function having no effect on the division potential or other performance requirement of the cell for the contemplated application. Hence, such compounds may be considered to be without appreciable detrimental effect on cell function for purpose of its use in this invention. Procedures are exemplified below for determining the effect on cell functions of potential importance to the practice of this invention, produced by compounds of the invention.

Two criteria must be met in selecting a cell binding medium in order to reproducibly bind compounds of the invention to the plasma membrane of cells without diminishing cell viability or otherwise producing a detrimental effect on desired cell function. The cell binding medium must (i) be at an iso-osmotic concentration as to not cause shrinkage or swelling and possible damage to the cells and (ii) allow for the compounds of the invention to be solubilized in such a manner that they are available at consistent concentrations to incorporate into the plasma membrane of the cells.

As noted above, the compounds of the invention have a lipophilic nature which allows them to become embedded into the plasma membrane of the cell and remain there in a stable manner. The very characteristics which allow the compounds of this invention to be used in cell labeling, namely, tendency to orient themselves preferably in the non-polar environment of the membrane and not transfer via the surrounding ionic media to neighboring cells, creates the problem of the application of such compounds to the cells in a manner which allows for reproducible binding. Solubility time course experiments have shown that the compounds which serve to stably label the plasma membrane when solubilized in ionic solutions, (e.g., phosphate buffered saline, culture medium, etc.) tend either to form micelles or aggregates which can be precipitated. Consequently, the concentration of such compounds in a form adequate for binding to the plasma membrane is decreased and time dependent, thus resulting in reduced incorporation of the compound into the plasma membrane. Moreover, such binding as a results occurs in a non-consistent manner.

The iso-osmotic characterization of the binding medium may be performed using commercially available instrumentation (μOsmette, Precision Instruments, Sudbury, Mass.). This instrumentation precisely measures freezing point depression of a given solution, which provides information as to the concentration or osmotic pressure of the solution. An iso-osmotic solution will support a given cell without having any effect on its volume. Osmolarities of solutions which will support mammalian cells normally range between 260 and 340 milliosmols. By these measurements the concentration of a given solution, which can be used to apply the compounds of this invention, can be adjusted such that an iso-osmotic solution is obtained. The binding medium should also be isotonic for the bioparticle to which the compound is to be bound.

The second criterion for selection of a suitable medium for binding of said compounds requires experimental evaluation of the actual stability of said compounds in a given medium and can be characterized by compound solubility determination (CSD). In making such determination, the compound is prepared in an ethanol stock at a concentration of $2 \times 10^{-3}$M. Ten milliliters of a working solution is prepared from the ethanol stock so that a final concentration of 1 to $4 \times 10^{-5}$M is obtained. One milliliter of this solution is then aliquoted into each of six 1.5 ml micro-centrifuge tubes. One tube is microfuged at 10,000×g at time points equal to 0, 15, 30, 45, 60, and 120 minutes. A 100 ul aliquot is removed from the supernatant and diluted into 3.0 ml of ethanol for each time point sample. Fluorescent compound concentrations in the supernatants over the 2 hour time point can be determined by observing the fluorescence units obtained from a spectrofluorometer using the peak excitation and emission wavelengths for the compound of interest.

With radioisotopic compounds the same experimental procedure is applicable and the results can be determined by using beta or gamma counters. In all cases, the amount of the compound of the invention in the supernatant of said iso-osmotic solution at each time point is compared to a sample of such compound using ethanol as a solvent, which, although not suitable for labeling cells, serves to allow for the maximum compound solubility (total). The percent solubility of the compound is determined in each of the composition formulations, and is monitored over the 2 hour time course. Any composition formulation which shows more than a 20% deviation over the 2 hour time points will not provide for reproducible binding to the plasma membrane by the compound of interest.

Several factors enter into the determination of the concentration of the compound of the invention used to bind to the plasma membrane of cells. The intended effect to be produced by the compound, the cell type being labeled, and the method of detection are primary considerations. Using fluorescent compounds, for example, to follow cell growth or divison, the highest concentration possible is desired which will not cause quenching of said compounds and which will allow for a large dynamic range between labeled and non-labeled cell types. There is, however, an upper limit to the excessive incorporation of the compound into the plasma membrane. Using tissue culture cells, concentration ranges from $1 \times 10^{-6}$M to $1 \times 10^{-5}$M allow for the monitoring of at least 6 cell divisions of the population while concentrations in excess of $4 \times 10^{-5}$M have been shown to produce some cytotoxic effect on certain cell types being labeled.

With the radio-isotopic compounds different concerns must be addressed. Here the determination of the concentration of the compounds for application to the plasma membrane is primarily dependent on the sensitivity of the method of detection and correspondingly the energy of the radio-isotope being used. The time required for labeled cells to reach their target site also becomes important and in the ideal situation a balance exists between all of these factors. For diagnostic purposes, the goal is to incorporate enough of the radio-binding compound to allow for detection of the location of the labeled dells once they have reached the location of interest, while minimizing the amount of radiation exposure to the patient. The half-life and the energy emitted by the radio-isotope being used, as well as the number of labeled cells necessary to image or diagnostically locate the site of interest, all concomitantly contribute to the optimum or minimum concentration for cell binding.

Use of the compounds of the invention for therapeutic purposes involves concerns similar to those applicable to the fluorescent applications. The primary goal is to incorporate as much of the therapeutic agent into the cell membrane as possible. By maximization of the incorporated therapeutic agent into the plasma membrane of the cell, fewer cells would be required to reach the desired location to exert the desired effect. Once again, the amount incorporated may only increase to such a level that no negative alterations are noted in the carrier cell with respect to viability or capability of the cells to migrate to the desired location.

Representative methods of use of the compositions of the invention will now be described with reference to particular diagnostic and therapeutic applications.

Cell Labeling With Fluorochrome

Fluorescent compounds of this invention are applied to carrier cells in the absence of serum and other lipid-containing materials. Cells are removed from the body or taken from culture and washed to be free of serum. They are suspended in a composition of the invention which includes the iso-osmotic regulating agent but not in ionic solutions and an appropriate concentration of the fluorescent compound ($10^{-5}$ to $10^{-7}$M). Binding of the compound to the cells is generally complete within ten minutes and the binding reaction is stopped with the addition of autologous or heterologous serum. The cells are then washed in serum containing media (5–10% v/v) and placed into culture or injected into the animal, depending on the application.

The procedure for cell binding of compounds of the type described herein is described in further detail in the aforementioned U.S. patent application Ser. No. 925,192, the entire disclosure of which is incorporated by reference in the present specification as though written out herein in full.

Another method involves suspension of the fluorescent compound in saline to allow for micelle formation. The cells are then placed into the resulting suspension and the phagocytic cells (for example, monocytes, macrophages and neutrophils) will preferentially become labeled. In this way, it is possible to selectively direct the stain to the phagocytic cells.

Binding of a fluorochrome to transplanted bone marrow cells in the manner just described allows the determination of whether the cells migrate to a specific site of hematopoesis and, after detection at such site, whether cell division occurs there. A fraction of the donor's cells are subjected to density gradient sedimentation and the mononuclear cells are isolated, washed and labeled with the non-ionic application of fluorescent compound. The washed fluorescently labeled cells are injected into the recipient intravenously. At periodic intervals (2–4 hours) blood is removed by venipuncture and the percent of labeled cells is determined, e.g., using flow cytometry. The rate of disappearance of the cells from the circulation is a measure of the speed at which the cells are homing to centers of hematopoeitic activity. Additionally, bone marrow aspirates are taken at weekly intervals and then subjected to density gradient sedimentation. The mononuclear population obtained by this method is then exposed to a "cocktail" of monoclonal antibodies which bind to myeloid cells and are labeled with a fluorescent color different from the tracking compound. Using monoclonal fluorescence and flow cytometry, it is then possible to determine the fluorescent intensity of the tracking dye on those cells which are of myeloid origin. If the intensity of the tracking dye on the myeloid cells diminishes with time, then a growth rate can be determined for these cells. This procedure is described more fully in the aforementioned U.S. patent application Ser. No. 925,445, the entire disclosure of which is incorporated by reference in the present specification as though written out herein in full. Furthermore, the fact that the cells are growing is of clinical significance to demonstrate that the transplanted marrow is repopulating. Similar methods are used for evaluating other cell lineages, if desired.

Another application of the fluorescent-labeled cells is in chemosensitivity testing. After a primary tumor is excised, the cells are dispersed and labeled with a fluorescent compound of the invention. The cells are then placed into wells and the fluorescence intensity of the cells is determined, e.g., by quantitative cytometry. As the cells divide, the fluorescence intensity will diminish and this loss of fluorescence can be determined with a cytometer at various intervals after placing the cells in culture. The rate of loss of fluorescence in the presence or absence of varying concentrations of a chemotherapeutic drug is a measure of cytostasis caused by the drug. Additionally, a dye exclusion test can be used simultaneously to determine the level of cytotoxicity. If the tracking dye is green fluorescing, then the red dye propidium iodide could be used for cytotoxicity measurements. Furthermore, it is possible to use monoclonal antibodies which specifically bind tumor cells in combination with the dyes just described to monitor cytostasis and cytotoxicity on tumor cells and normal cells independently.

Fluorescent-labeled cells may also be used in monitoring the fate of transfused red blood cells to determine whether the patient is experiencing post-surgical bleeding, or whether there is an autoimmune hemolysis. To achieve this goal, an aliquot of the red cells to be transfused is labeled with the fluorescent form of the tracking dye. The fluorescent cells are transfused with the remainder of non-fluorescent cells and immediately post-surgery a blood sample is taken, e.g., by venipuncture. The percent fluorescent cells may be determined using flow cytometry or fluorometry. At periodic intervals additional blood samples are taken and the percent labeled cells is determined. If the patient is experiencing autoimmune hemolysis, the ratio of fluorescent to non-fluorescent cells will not change even though the hematocrit may be dropping. If the patient is experiencing autoimmune hemolysis, the ratio of fluorescent to non-fluorescent cells will drop because the antibody will be directed only against the transfused cells.

Radio-Imaging

The compounds of this invention which have the capacity of binding to the lipid phase of the membrane and to chelate Indium-111 or Technetium-99 m, or other radio-imaging atoms, are first bound to the radioactive ion to form a stable complex. The complex is separated from the free radioisotope, then transferred to an iso-osmolar solvent that is non-ionic. The cells are placed together with the chelator-radioisotope complex in this solvent and the complex is then bound to the cell membrane. The binding reaction is stopped with autologous or heterologous serum. The cells (or viruses) are washed free of unbound chelator-radioisotope complex and the cells (or viruses) are ready to be injected into the animal and the final location detected using a gamma camera.

Such compounds may be used to locate the site of occult infection via binding to a neutrophil, the primary phagocytic leukocyte of the blood. When attempting to locate the site of occult infection in a symptomatic individual, leukocytes are isolated from the individual's blood. These cells are then labeled with Indium or Technetium, generally as described above and injected intravenously. Within the next 48 hours, the radioactive-labeled neutrophils migrate to the site of the infection where the gamma emission can be detected using a gamma camera.

In another application of this technology, a platelet may be tracked to the site of fresh plaque on arterial walls or to a thrombus. When attempting to locate the site of plaque formation in a symptomatic, or asymptomatic individual, platelets are isolated from the individual's blood using standard gradient techniques. These cells are then labeled with Indium or Technetium, as described, and injected intravenously. A suitable procedure for binding compound of the type described herein to platelets is provided in the aforementioned U.S. patent application Ser. No. 925,192. Within the next 48 hours, the radioactive labeled platelets migrate to the site of the plaque formation on arterial walls, where the gamma emission can be detected using a gamma camera.

In another application of the radio-imaging methodology described herein, a tumor infiltrating lymphocyte may be isolated from a primary lesion, expanded in Il–2, labeled with a tracking radioisotopic form of a compound of the invention and the washed cells are injected intravenously. In this application, the assumption is made that a tumor infiltrating lymphocyte is at the tumor site because of an ability to detect the presence of tumor cells and then migrate to that site. Furthermore, the frequency of tumor tracking lymphocytes in circulation is very low, and by using the lymphocytes found in the primary tumor, advantage is taken of the body's own mechanism to concentrate these tracking cells. These cells are grown in the presence of a lymphocyte specific growth factor (Il–2) and in the presence of tumor cells. The in vitro growth of lymphocytes expands their number so that a portion of these cells is radioactively labeled and injected while the remainder is placed into dimethyl sulfoxide (DMSO) and serum and frozen at liquid nitrogen temperatures for preservation. These frozen cells can be thawed, radioactively labeled and injected periodically, and thereafter imaged using gamma imaging techniques to locate the position of metastatic lesions.

Radio-Isotope Labeling

While it is possible to use chelators to bind to radioactive metal ions, it is also possible to make fluorescent or non-fluorescent compounds of the formula $R-B-R_1$, wherein radio-isotopic atoms are constituitive to the molecule. For example, radioactive iodine, carbon, nitrogen, sulphur, phosphorus or selenium may be incorporated into the compounds of the invention. Compounds emitting gamma rays of sufficient energy may be detected using gamma scintigraphy. For these radionuclides, all of the applications discussed above under the heading radio-imaging can likewise be accomplished. If the isotope is a low energy non-penetrating beta emitter, then the compound can be used in research applications using standard beta counting techniques.

Magnetic Resonance Imaging

The compounds of this invention which have the capability of binding to the lipid phase of the membrane and to chelate Gadolinium or other MRI contrast enhancing agents, are first bound to the ionic species of the selected metal to form a complex. The complex is separated from the free MRI contrast agents and then transferred to an iso-osmolar solvent that is non-ionic. The cells to be tracked are introduced into the solvent containing the chelator-ion complex, which becomes bound to the plasma membrane of the cells. The binding reaction is stopped with autologous or heterlogous serum and the washed cells are ready for use in magnetic resonance imaging applications. Compounds of the type just described enable detection of the site of occult infection. When attempting to locate the site of occult infection in a symptomatic individual, leukocytes are isolated from the individuals' blood. These cells are then labeled with a chelator-gadolinium complex, as described, and injected intravenously. Within the next 48 hours, the contrast agent labeled neutrophils migrate to the site of the infection where they can be detected by magnetic resonance imaging.

In another MRI application of the invention, a platelet may be tracked to the site of fresh plaque on arterial walls or thrombus. When attempting to locate the site of plaque formation in a symptomatic, or an asymptomatic individual, platelets are isolated from the individual's blood using standard gradient techniques. These cells are then labeled with a chelator-gadolinium complex, as described, and injected intravenously. Within the next 48 hours, the contrast agent labeled platelets migrate to the site of the plaque formation on arterial walls, where they can be detected by magnetic resonance imaging.

In another MRI application of the invention, a tumor infiltrating lymphocyte may be isolated from a primary lesion, expanded in I1–2, labeled with a magnetic resonance sensitive isotope and injected intravenously. In this application, the assumption is made that tumor infiltrating lymphocytes are at the primary tumor site because of an ability to detect the presence of tumor cells and that they are capable of migrating to the site of a metastasis. Furthermore, the frequency of tumor tracking lymphocytes in circulation is very low and by using the lymphocytes found in the primary tumor, use is made of the body's own mechanism to concentrate these tracking cells. The cells grown in the presence of a lymphocyte specific growth factor (I1–2) and in the presence of tumor cells. The in vitro growth of lymphocytes expands their number so that a portion of these cells are isotopically labeled and injected while the remainder are placed into DMSO and serum and frozen at liquid nitrogen temperatures for preservation. These frozen cells can be thawed, isotopically labeled and injected at many intervals after the initial growth period. The labeled tumor infiltrating lymphocytes are then injected, whereby they migrate to the site of metastatic tumors and can be detected by magnetic resonance imaging.

Isotopic Therapeutic Applications

The compounds of this invention which have the capability of incorporating into the lipid phase of the membrane and to chelate ions which are radioactive and emit high linear energy transfer (LET) radiation, can be used to deliver radiation therapy to the site of disease. These chelators are first bound to the appropriate radioactive ion (e.g., $^{67}$Cu, Yt, alpha emitters) to form a complex. The complex is separated from the free ions and then transferred to an iso-osmolar solvent that is non-ionic. The cells to be used as therapeutic carrier vehicles are introduced into the solvent containing the chelator-ion complex, which becomes bound to the plasma membrane of the cells. The binding reaction is stopped with autologous or heterologous serum, and the washed cells can be injected into the animal to track to the disease site for delivery of their radiation therapy.

In another application of this radiotherapeutic delivery technique, a tumor infiltrating lymphocyte may be isolated from a primary lesion, expanded in I1–2, labeled with the radiotherapeutic complex and injected intravenously. This application also relies on the capability of tumor infiltrating lymphocytes to detect the presence of tumor cells and then migrate to a metastatic site. These cells are grown in the presence of a lymphocyte specific growth factor (I1–2) and in the presence of tumor cells. The in vitro growth of lymphocytes expands their number so that a portion of these cells are isotopically labeled and injected. The labeled cells track to the site of metastatic disease, and emit radiation which kills the metastatic tumor cells.

Cell Targeting by Binding Specific Proteins to Cell Membranes

In another embodiment, the compounds of the invention incorporate proteinaceous substances, including proteins, glycoproteins, lipoproteins or peptides as the bio-affecting moiety. These compounds are formulated containing the iso-osmotic regulator which is compatible with their solvation and cell viability. The cells are placed into the cell binding medium whereupon the hydrocarbon chains of said compounds become embedded into the plasma membrane and place the protein onto the surface of a specific cell type.

The procedure just described may be used to bind monoclonal antibody to human fibrin to the surface of a tracking cell, e.g., red cell. The antibody-bound red cell is then isotopically labeled, as described above, using the radio-imaging compounds or the magnetic resonance imaging compounds. This doubly labeled (anti-fibrin+isotope) cell may be injected into a patient whereby the cell migrates to the site of a fibrin clot and can be imaged using standard gamma scintography or nuclear imaging.

In another application of this invention a monoclonal antibody to human cell surface tumor antigens may be bound to the surface of a tracking cell, e.g., monocyte or lymphocyte. The resultant cell is then isotopically labeled, as described above, using the radio-imaging compounds or the magnetic resonance imaging compounds. This doubly labeled (anti-tumor cell+isotope) cell is injected into a patient whereby the cell tracks to the site of a tumor and can be imaged using standard gamma scintography or MRI.

In another application of this technology (R-tPA-R$_1$) is applied to the surface of a tracking cell (e.g., red cell). The same cell is then isotopically labeled as described above using the radio-imaging compounds or the magnetic resonance imaging compounds. This doubly labeled (tPA+ isotope) is injected into a patient whereby the cell tracks to the site of a fibrin clot and can be imaged using using standard gamma scintigraphy or nuclear imaging. This same general protocol could be utilized without the addition of the isotope and administered to deliver more tPA to a fibrin clot site to produce a therapeutic action.

In another application of this invention, a monoclonal antibody which binds to human fibrin is bound (R-Mab-R$_1$) to the surface of a cell (e.g., red cell). The same cell is then also bound with a fibrinolytic compound (tPA, Streptokinase, urokinase) of the form (R-tPA-R$_1$, etc.). Thus, the monoclonal antibody increases the ability to bind to fibrin and after binding delivers a large number of therapeutic fibrinolytic compounds.

Protein Coupling to Cells for Vaccine

In another application of this invention, a protein, glycoprotein, lipoprotein or peptide to which antibody production is desired, is bound (R-protein-R$_1$) to the surface of a cell (e.g., red cell, monocyte). This cell is then injected in the presence or absence of adjuvant. The timing interval between injections will depend upon the nature of the antigen (protein) but generally 10 million cells may be injected each time at intervals of not less than two weeks.

Antibody levels to the antigen are monitored with standard Elisa procedures. Cellular immune levels can be measured on immunizing cells.

Alterations in Migration Patterns by Modifying Cell Surface

In another application of this technology, sialic acids (R-sialic acid-R$_1$) or glycosaminoglycans (R-glyamgly-R$_1$) can be placed onto the plasma membrane of a cell. The specific compound is placed into iso-osmotic media as described hereinabove. Red cells, for example, are placed into the solution, resulting in binding of the compound to the plasma membrane. The reaction is stopped with the addition of serum, after which the cells are washed in saline containing medium and are ready for injection.

Red cells traverse the circulation and as immature cells they have a large amount of sialic acid on their surface. As the red cell ages, the amount of sialic acid per cell is reduced making it possible for the splenic and liver macrophages to recognize red cell membrane antigens, thereby removing them from circulation. By appropriately increasing the amount of sialic acid into the membrane of a red cell, it may increase the life of the red cell in circulation. The ability to increase the lifetime of a red cell may be advantageous for a transplant patient or for a patient with anemia. When bone marrow transplant patients receive the transplant, it is several weeks before they are capable of making their own red blood cells. By using this technology to prolong the lifetime of their own red cells, the patient can be given several marrow transplants, if need be, without having bouts of anemia.

In the case of the anemic individual, the anemia may result from a decrease in the lifetime of the red cell or a decrease in the rate of production of red cells. In either case, to increase the lifetime of the red cell will reduce the anemia.

Delivery of Photodynamic Compounds for Therapeutic Action

Photodynamic therapy for the cure of cancer is an area of intense research (Proceedings of SPIE-The International Society for Optical Engineering Volume 847, "New Directions in Photodynamic Therapy", Douglas C. Neckers, Editor; October 1987). Many of these compounds are of the phthalocyanine class or the hematoporphrin class. All absorb light in the 600–800 nm region and produce excited state oxygen in the process. According to existing protocols, the compounds are administered orally or parenterally and the specificity of binding to tumor cells is totally dependent upon the chemistry of each specific molecule. Once delivered to the tumor cell, the compounds are excited with light whereby excited state oxygen is produced and the tumor cells are killed.

Using the methodology of this invention, a derivative of the compound (R-Photodynamic compound-$R_1$) is made and then dissolved in the iso-osmotic solution. Tumor tracking cells (e.g., tumor infiltrating lymphocytes) are labeled with these compounds and the cells are injected into the patients. The tumor tracking cells then migrate to the site of the micromtatasis. Within 48 hours the patient is exposed to high intensity light in the region where the photodynamic molecule absorbs and the excited state oxygen produced will kill the tumor cells. Furthermore, the tracking cell will be killed and this should generate an inflammation whereby more immune cells converge to remove the dead cells, increasing the toxicity to tumors. In this method of delivery of photodynamic action, the tracking cells are responsible for the specificity of tumor kill.

The following examples are provided to describe the invention in further detail. These examples are intended to illustrate certain aspects of the invention and should in no way be construed as limiting the invention.

EXAMPLE 1

Determinations of Effects Produced on Cell Function by Binding of Compounds to Plasma Membrane a. Effect on Growth Rate of Cells To measure the effect of compounds of the invention on cell growth rate, cells must be first exposed to varying concentrations of a selected compound.

To this end, logarithmically growing Yac-1 cells were washed once in PBS and resuspended in a solution of the fluorochrome 3,3'-ditetradecyloxacarbocyanine (DiO-C14 (3)) ($10^{-5}$M) at a concentration of $10^6$–$10^7$ cells/ml for 5 minutes at room temperature. The binding reaction was terminated by adding an equal volume of fetal calf serus (FCS) and the cells were pilleted at 400×g for 5 minutes, washed (3×) and resuspended in complete media. Fluorescence intensity measurements were made using a Coulter EPICS 753 flow cytometer. 200 mW of 488 mm light was used to excite the dye and the green fluorescence of propidium iodide negative cells was measured using a 525 nm band pass interference-type filter.

In FIG. 1, the fluorescence intensity of YAC-1 cells stained with the $DiOC_{14}(3)$, recorded in FIG. 1, is extremely bright as compared with the unstained controls. Similar results have been obtained with other fluorescent compounds of this invention. A large dynamic range between fluorescence positive and fluorescence negative cells is shown in FIG. 1A. The range of the staining reaction is so large that the fluorescence intensity must be plotted on a semi-logarithmic scale.

Figure 1B:
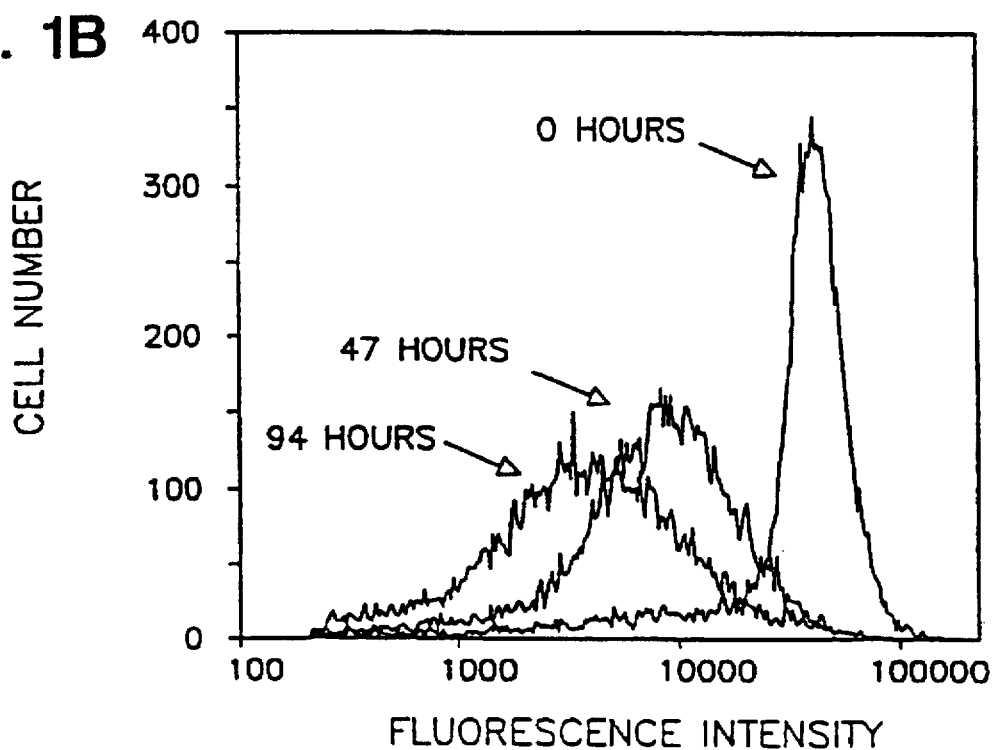

To monitor the growth rate of cells, DiO-C14-(3) bound cells were placed into the incubator in complete culture media (DMEM High Glucose+20% FBS) and analyzed daily using flow cytometric techniques. The instrument was aligned daily and intensity settings reproduced using fluorescent microbead standards. From each fluorescence profile the mean fluorescence intensity and standard deviation were determined. A decrease in the fluorescence intensity is observed as a result of these determinations (FIG. 1B).

Figure 2:
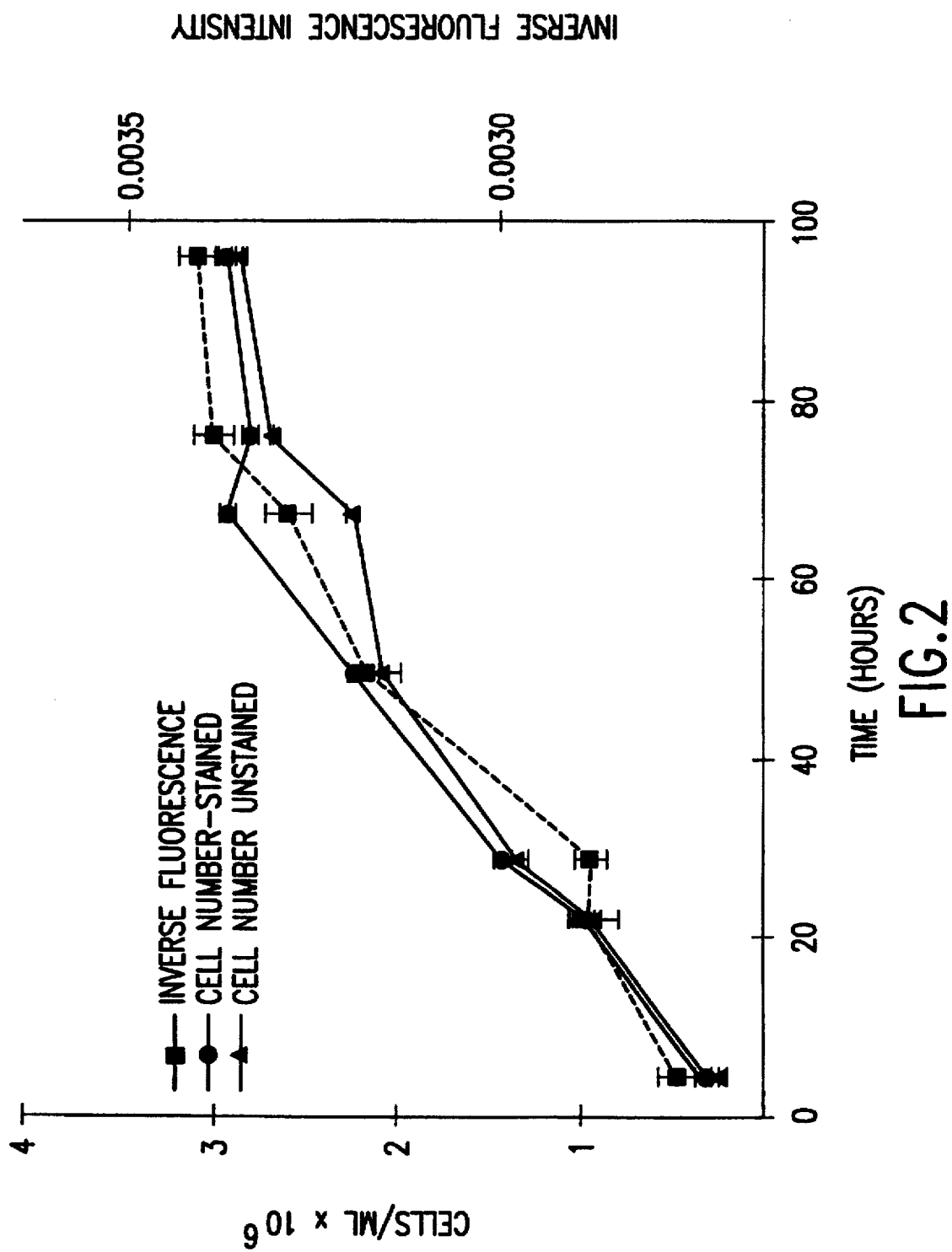
FIG. 2 graphically represents cell number and inverse fluorescence intensity measurements as a function of time using DiO-C14-(3)-labeled and unlabeled Yac-1 cells.

In FIG. 2, growth rates are compared for stained and unstained YAC-1 cells. Separate flasks of DiO-C14-(3) labeled and non-labeled control cultures (Yac-1) were each set at $2\times10^5$ cells/ml at time zero. Cell counts were obtained using a Coulter ZBI cell counter (Coulter Electronics, Inc. Hialeah, Fla.). Fluorescence intensity measurements were determined as described above with reference to FIG. 1. Mean log fluorescence intensities were determined for each time point and the inverse was calculated and plotted. Standard deviations were calculated and plotted at each time point having been determined on quadruplicate samples because cell growth kinetics are exponential in nature, a semilog plot of the fluorescence intensity is linear during the log phase of growth as shown in FIG. 2. As can be seen from FIG. 2, the growth rate is the same for stained and unstained cells. Furthermore, each day the average fluorescence intensity was determined for the stained culture. The inverse of the fluorescence intensity is plotted alongside the cell growth data in FIG. 2 and it is clear that in a logarithmically growing culture, the decrease in fluorescence intensity is directly proportional to the cell growth rate.

b. Effect on Binding Affinity for Target Cells

Another cell function which is important in certain applications of the invention is the ability of a lymphocyte (NK-cell) to recognize, bind to and kill a target tumor cell. In a number of embodiments of this invention it is desirable to track an effector NK-cell to the site of a tumor. To determine if a compound of this invention has any detrimental effect on this function, effector cells or target cells are bound with the compound.

Figure 3:
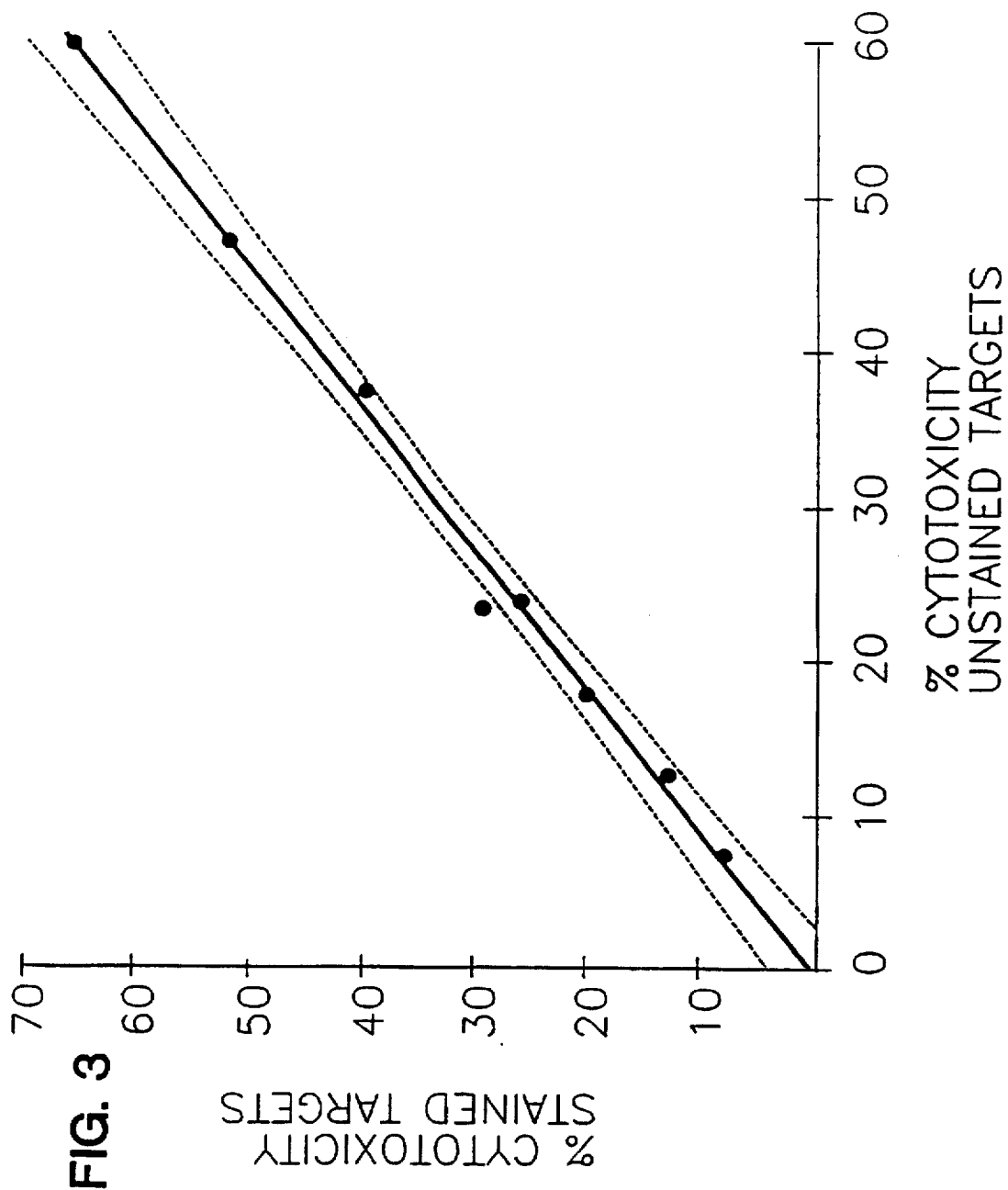
FIG. 3 is a graphical representation showing the correlation with respect to cytotoxicity of DiO-C14-(3) stained and non-stained Yac-1 targets.
Figure 4:
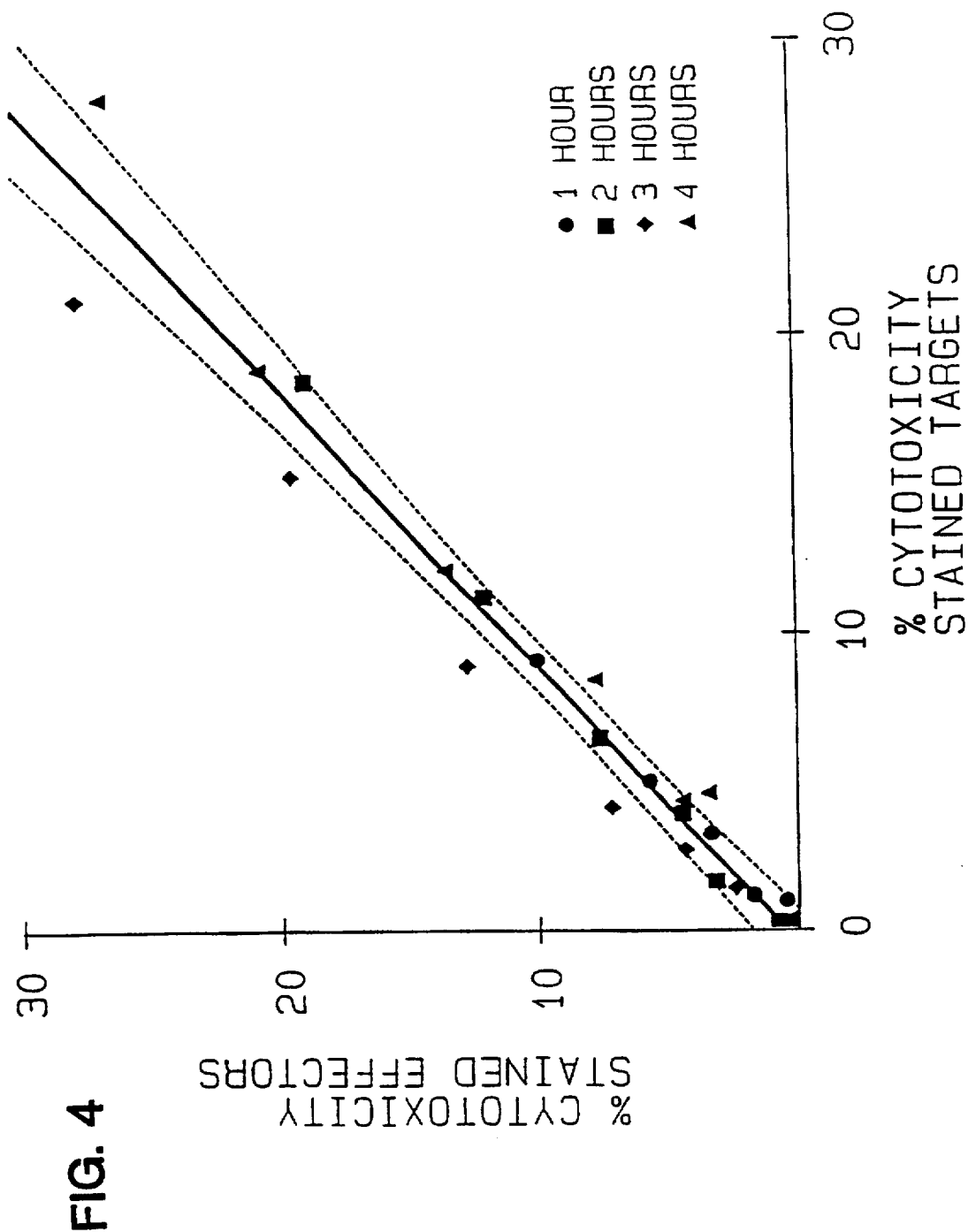
FIG. 4 is a graphical representation showing the correlation with respect to cytotoxicity of effector/target staining using DiO-C14-(3) stained Yac-1 targets and unstained Poly I:C treated NK-preps, versus unstained Yac-1 targets and stained Poly I:C treated NK-preps.

The standard assay for cell mediated cytotoxicity (Brunner, K. T., Mauel, J., Cerottini, J. C., Chapuis, B., Immunol., 14, 181, 1968) is to label the target cells with $^{51}Cr$ and wash the cells free of all unbound $^{51}Cr$. The effector cells are placed in contact with the target cells at varying ratios and when the target cells are killed by the effector cells, the $^{51}$Cr is released from the cell into the medium. The level of cytotoxic kill is correlated to the amount of $^{51}$Cr released into the medium, as determined by a gamma counter. To determine the affect of the compounds of this invention on cell mediated cytotoxicity, the $Cr^{51}$ release is measured for unlabeled cells, labeled effector cells and labeled target cells. The results of such measurements using DiOC14(3) labeled and unlabeled Yac-1 targets is shown in FIGS. 3 and 4. Values for effector/target ratios of 50:1, 25:1, 12:1 and 6:1 of both Poly/I:C and saline treated effectors to unstained Yac-1 targets are represented on the x-axis. Values of % kill for the same ratios of Poly I:C and saline treated effectors to stained Yac-1 targets are represented on the y-axis. Ninety-five percent confidence intervals are represented by the dashed lines. From FIG. 3, it can be seen that chromium release (% cytotoxicity) is the same whether the targets are stained with DiOC14(3) or unstained. Values for % kill by Cr(51) release calculated for DiO-C14-(3) labeled Yac-1 targets and non-labeled Poly I:C treated NK-preps are represented on the x-axis. The percent kill by chromium release given on the y-axis represent values obtained using non-stained Yac-1 targets and DiO-C14-(3) stained Poly I:C treated NK-preps. Samples were taken at times of 1, 2, 3 and 4 hours for both sample sets. E/T ratios used were 50, 25, 12, 6, 3, and 1.5 to 1. FIG. 4 shows that the chromium release (% cytotoxicity) is the same whether the target cells or the effector cells are stained. These results indicate that the function of cell mediated cytotoxicity is unchanged after labeling either effector or target cells with the fluorochrome.

The above described cell mediated cytotoxicity assay demonstrates that the cell labeling does not affect the ability of the effector cell to find, bind or kill the target cell. It is possible that some other function not tested may be affected, but since the functions of interest were unaffected, it may be concluded that there were no appreciable adverse effects on the function of cell mediated cytotoxicity.

EXAMPLE 2

Determination of Membrane Retention Coefficient

The membrane retention coefficient (MRC) provides information regarding how well a given compound is retained in the plasma membrane of a carrier cell and is determined as described below.

Generation of red blood cell ghosts for use as a model membrane is achieved by centrifuging whole blood at 300×g for 15 minutes, removal of the plasma and resuspension of the cell pellet in 0.83% (weight to volume) ammonium chloride. The ghosts are pelleted from the ammonium chloride by centrifuging at 10,000×g for 10 minutes. This ammonium chloride washing procedure is repeated a minimum of five times to insure that complete release of hemoglobin from the cells has occured. The ghosts are labeled with the compound in question at a concentration allowing for detection of the labeled ghosts by instrumental analysis or fluorescent microscopic methods, and at a concentration which would be used to label cells for a specific application as described above. For these determinations stock solutions of the compounds in question are prepared in ethanol at a molar concentration of $2\times10^{-3}$, and working dilutions of the compounds were prepared in iso-osmotic sucrose (52 grams/500 milliliters distilled water). After incubation of the ghosts at an approximate concentration of $1\times10^9$ ghosts/ml in the working dilutions of the compounds for 10 minutes, the samples are centrifuged at 10,000×g to pellet the ghosts and the staining solution was aspirated from the samples. The labeled ghosts are resuspended in 1 ml of phosphate buffered saline solution containing 10% fetal bovine serum (PBS-FBS). Triplicate 20 ul aliquots are removed from each sample for the determination of the amount of total compound present. The samples are centrifuged as described above and triplicate 20 ul aliquots are removed from the supernatant for quantitative determination of amount of compound present.

After sampling, the supernatant is aspirated and the red cell ghost pellet is resuspended in 1.0 ml of the PBS-FBS, which is once again sampled as described above. This procedure is repeated at least six times, allowing for detection of rapidly released compounds and is monitored after times equal or greater than 24 hours to allow for the detection of more slowly released compounds. For the determination of the amount of compound present in each sample, the 20 ul aliquots are extracted into 3.0 ml of n-butanol by shaking. The samples are centrifuged at 3000×g to remove membrane debris and the butanol fractions are assayed for compound concentration. Fluorescent compounds are assayed in this manner using peak excitation and emission wavelengths for the particular compounds being assayed to determine the fluorescence units for each sample. Radiolabeled compounds do not require butanol extraction and could be assayed directly using beta or gamma counting instrumentation.

The determination of the amount of compound present in each sample as described above allows for the calculation of the MRC for each washing or fixed time point. The value is obtained by the following formula:

$$((C_T-C_S)/C_T)*100$$

where $C_T$ represents the amount of compound present (in units determined by the method used to assay the compound) in the total sample and $C_S$ represents the amount of compound present in the supernatant sample for that particular time point. The comparison of the MRC values defines criteria for identification of the compounds of this invention, these criteria being: 1) the MRC values determined for each washing steps should have a value of at least about 90 and 2) the percent difference between MRC values over at least a 24 hour time period should be less than about 10%. The data provided in Table I below are the results from one experiment and serve as an example of the MRC determination.

TABLE I

| MEMBRANE RETENTION COEFFICIENTS (MRCs) FOR CELL BINDING COMPOUNDS | | | | | | | | |
|---|---|---|---|---|---|---|---|---|
| COMPOUND | WASH 1 | WASH 2 | WASH 3 | WASH 4 | WASH 5 | WASH 6 | 24 HR | CHANGE IN MRC |
| DiI-C5-3 | 51.63 | 51.12 | 44.82 | 41.39 | 12.59 | 17.48 | 0.00 | 100.00% |
| DiI-C10-3 | 83.28 | 92.36 | 94.63 | 94.94 | 95.33 | 94.80 | 54.08 | 42.95 |
| DiI-C14-3 | 94.85 | 97.24 | 98.40 | 98.64 | 98.43 | 99.12 | 93.90 | 5.26 |
| PKH/CMPD 1 | 50.40 | 61.20 | 64.45 | 65.85 | 70.62 | 77.92 | 18.84 | 75.82 |

TABLE I-continued
MEMBRANE RETENTION COEFFICIENTS (MRCs) FOR CELL BINDING COMPOUNDS
| COMPOUND | WASH 1 | WASH 2 | WASH 3 | WASH 4 | WASH 5 | WASH 6 | 24 HR | CHANGE IN MRC |
|---|---|---|---|---|---|---|---|---|
| PKH/CMPD 2 | 90.69 | 94.74 | 96.28 | 96.74 | 96.41 | 97.17 | 53.81 | 44.62 |
| PKH-3 | 88.82 | 93.94 | 95.15 | 95.26 | 94.51 | 96.64 | 36.77 | 61.64 |
| PKH-4 | 94.42 | 96.96 | 98.03 | 97.93 | 97.92 | 98.34 | 96.90 | 1.46 |
| PKH-5 | 91.70 | 97.22 | 97.97 | 98.24 | 98.09 | 98.40 | 90.10 | 8.43 |
| PKH-6 | 94.69 | 98.24 | 98.32 | 98.78 | 98.96 | 99.73 | 97.65 | 2.08 |
| PKH-7 | 94.07 | 96.99 | 98.66 | 98.39 | 98.82 | 97.56 | 87.24 | 10.57 |
| PKH-8 | 97.35 | 98.47 | 98.16 | 98.99 | 99.01 | 99.46 | 97.90 | 1.56 |
| PKH-11 | 91.01 | 95.12 | 95.82 | 96.42 | 96.27 | 97.01 | 42.88 | 55.79 |
| PKH-13 | 95.97 | 97.51 | 98.32 | 98.48 | 98.71 | 98.88 | 98.27 | 0.61 |
Structures for the above compounds identified in Table I are set forth in Table II.
TABLE II
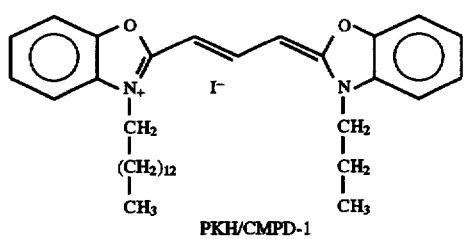
PKH/CMPD-1
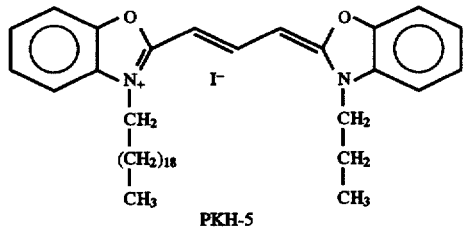
PKH-5
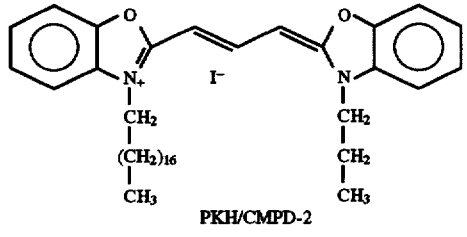
PKH/CMPD-2
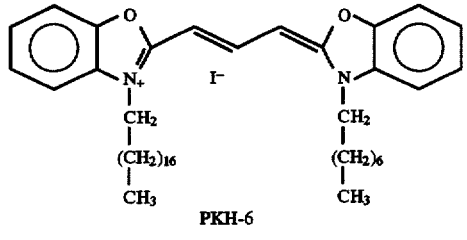
PKH-6
TABLE II-continued
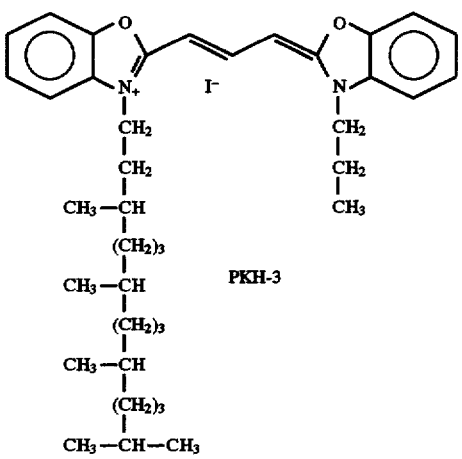
PKH-3
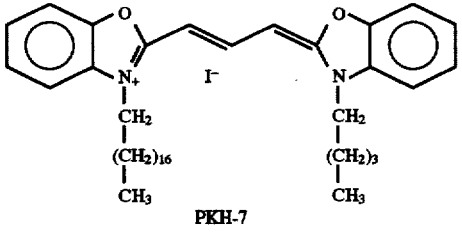
PKH-7
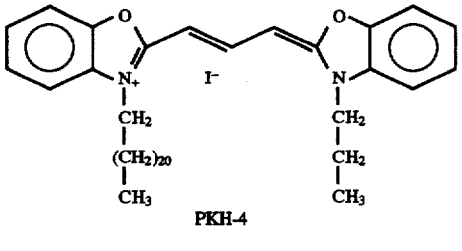
PKH-4
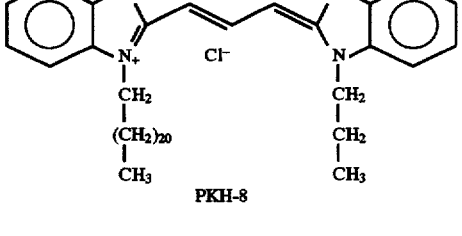
PKH-8

TABLE II-continued

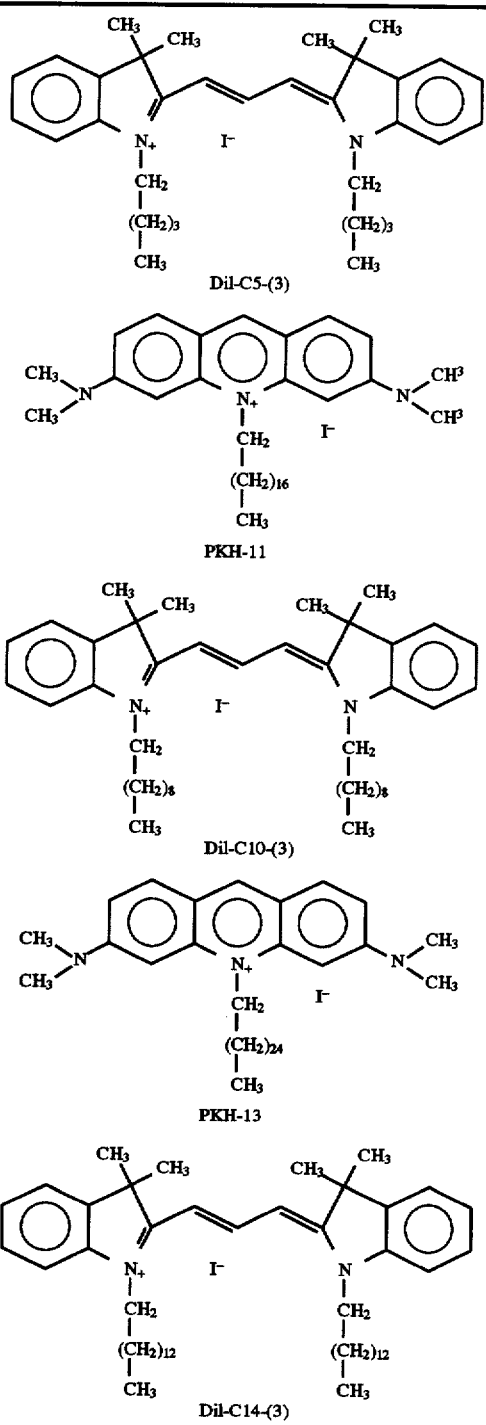

DiI-C5-(3)

PKH-11

DiI-C10-(3)

PKH-13

DiI-C14-(3)

Another procedure which may be employed to determine the cell binding capability of fluorescent compounds according to this invention is intercellular compound transfer analysis (ICTA). In performing this analysis, tissue culture cells, in this example Yac-1 cells, at a concentration of approximately $1\times10^7$/ml are labeled with $4\times10^{-6}$M of the compound of choice in iso-osmotic sucrose solution for 10 minutes. Staining was terminated with an equal amount of FBS and the cells were washed three times and resuspended in complete tissue culture media. Equal numbers of labeled and non-labeled Yac-1 cells were placed into culture flasks at a density of $4\times10^5$ cells/ml in 20 ml of fluid. The cells were cultured for 4 days at 37° C. in a 5% $CO_2$ atmosphere. An aliquot of each culture to be tested is removed daily for flow cytometric analysis. Percent labeled and fluorescence intensity was determined. The exciting and detection wavelengths for analysis are selected on the basis of the individual properties of the compound being tested.

Figure 5A:
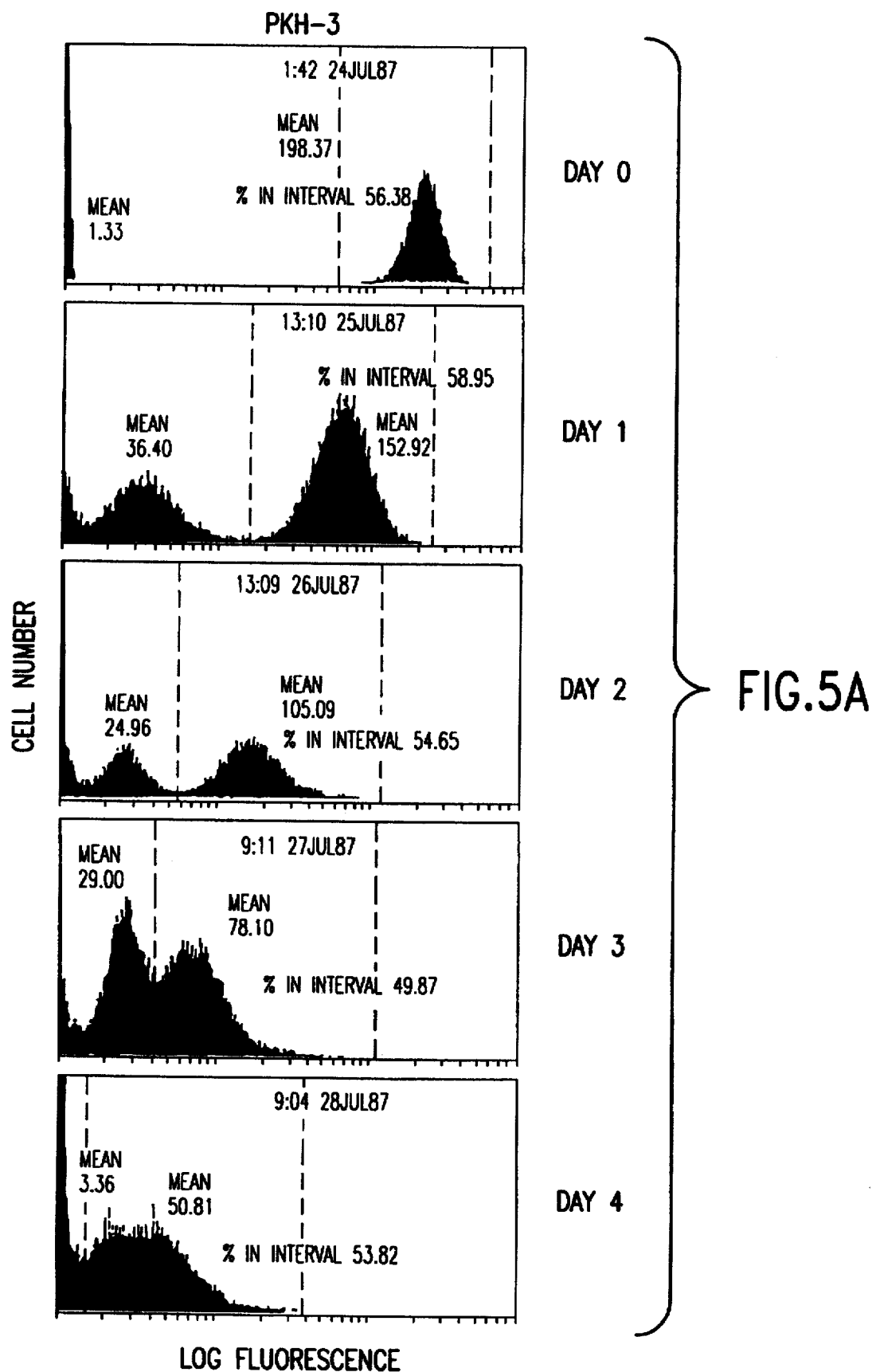
FIG. 5A–5C illustrates the cell binding stability of a compound of the invention as compared with two different fluorescent compounds with unacceptable levels of release from the plasma membrane of labeled cells.

A fluorescence histogram was generated for each of three test compounds and examples of such histograms are seen in FIG. 5. Initially, each histogram contains two populations: the left most population represents the non-labeled cells which were added into the culture, and the right hand population represents the compound labeled cells of the culture. If the labeled and non-labeled cells are placed in culture at a 1:1 ratio the percentage of cells represented in either of the peaks should be approximately 50%. It is important to monitor three attributes of the histograms over time: 1) the mean intensity of the positive or labeled population, 2) the mean autofluorescence intensity of the non-labeled population and 3) the percentage of positive or labeled cells in the culture. These three parameters serve to define whether the compound is stably retained in the membrane, thereby not transferring to other cells and serve to determine if the compounds produce a cytostatic and/or cytotoxic effect upon the cells to which they are bound. If transfer or leakage of the compound occurs, an increase in the mean intensity of the non-labeled population will be observed. In FIG. 5A, it is noteworthy that on Day 1, the fluorescent intensity of non-labeled cells (left peak) was significantly increased over Day 0, indicating that (PKH-3) leaks out of labeled cells (right peak, Day 0) and becomes incorporated into unlabeled cells. In Table I above, a percent change in MRC of 61% for this same compound is also indicative of cell leakage.

Figure 5B:
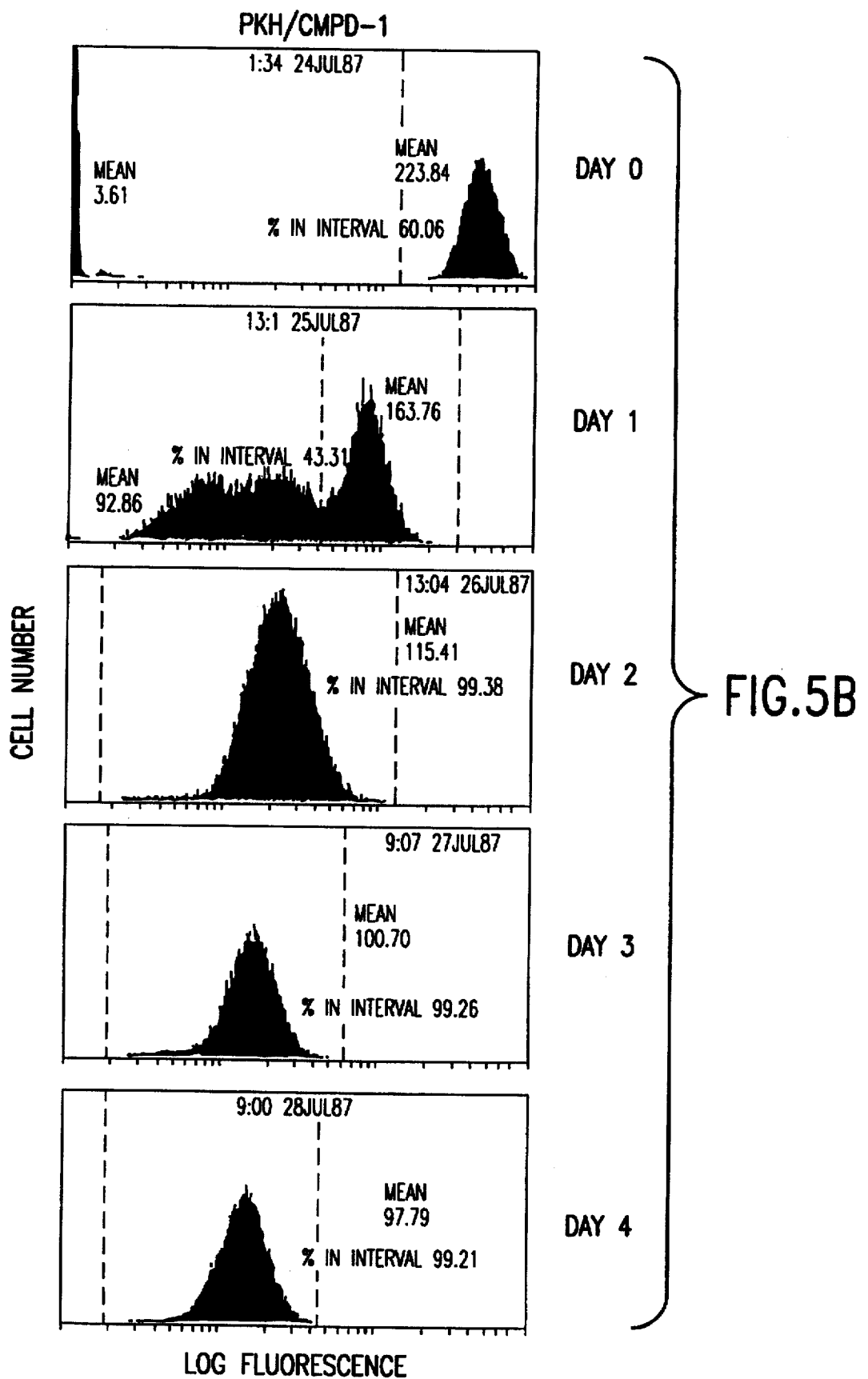

On the other hand, if the leakage rate is substantial a merging of the non-labeled and labeled populations will occur (FIG. 5B). If a cytostatic and/or cytotoxic effect has occurred the percentage of the labeled population will decrease from the value determined at time zero. FIG. 5B shows that the fluorescent intensity of non-labeled cells (left peak) is significantly increased over Day 0, indicating that 3,n-propyl-3'n-tetradecyloxcarbocyanine iodide (PKH/CMPD-1) leaks out of labeled cells. This is further evidence by a single peak on Day 2. Similarly, in Table I above, a percent change in MRC which of 76% for this same compound, is likewise of indicative cell leakage.

Figure 5C:
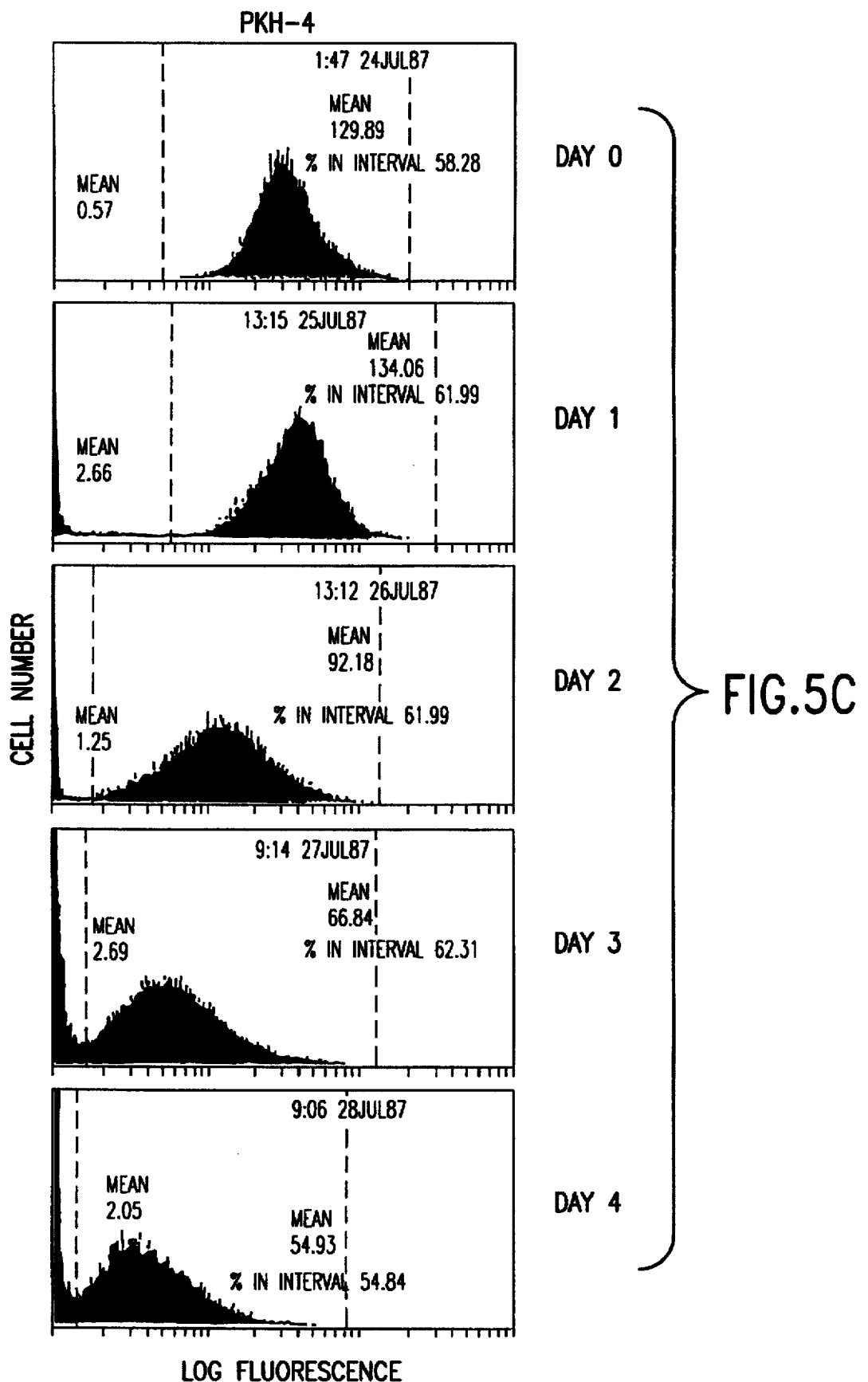

Fluorescent compounds usable in this invention have the following characteristics: 1) the percentage of cells in the labeled population over time does not significantly differ from the value obtained at time zero, 2) the mean intensity of the non-labeled population does not significantly increase over time, and 3) the mean intensity of the labeled population decreases in a manner which correlates with the growth characteristics of the cells. 3-n-propyl-3'-n-docosanyloxacarbocyanine iodide satisfies these criteria, as is evidenced by the histogram of FIG. 5C. Particularly noteworthy in FIG. 5C is the total separation of stained and unstained cell peaks for the five days of the experiment. Furthermore, the percent stained did not change appreciably. From Table 1 above, a percent change in MRC of 1.46% is reported for this compound indicating very stable binding to the plasma membrane. Additionally, the fluorescence intensity of labeled cells decreased daily as the cells divide.

The MRC values set forth in Table 1, above, show excellent correlation with the results obtained from intracellular compound transfer analysis, as described herein.

EXAMPLE 3

Preparation of Compounds a. 3-n-propyl-3'-n-eicosanyloxacarbocyanine Iodide 3-n-propyl-2-methylbenzoxazolium iodide was prepared according to the method described by J. Sims et al., Biochemistry, 13 (16) 3315-30 (1974)

A stirred mixture of the 3-n-Propyl-2-methylbenzoxazolium iodide (9.09 g, 30 mmol) and N,N'-diphenylformamidine (5.88 g, 30 mmol) in acetic anhydride (60 ml) was heated under reflux for 30 mins. The solution was then allowed to cool to room temperature, diluted with ether (300 ml) and refrigerated. The crystalline solid 2-($\beta$'acetonilido) vinyl-1-benzoxazolium-n-propyliodide was collected by filtration and recrystallized from ethanol/ether to give a brown crystalline solid (4.77 g, 35%), m.p. 209°-210° C. Found, C, 53.58%; H, 4.81%. N, 6.26%. $C_{20}H_{21}O_2N_2I$ requires C, 53.58%; H, 4.72%; N, 6.25%. v max; 3100-3000, 3000-2800, 1721, 1616, 1589, 1217, 763 and 700 cm$^{-1}$. $^1$Hnmr, $\delta$, 9.75 (d, J=14 Hz, 1H); 7.84-7.45 (m, 9H); 5.44 (d, J=14 Hz, 1H); 4.49 (t, J=7 Hz, 2H); 2.12 (s, 3H); 0.868 (t, J=7.4 Hz, 3H).

To a stirred solution of eicosanol (5.0 g, 16.70 mmol) and triethylamine (4 ml) in methylene chloride (80 ml) was added dropwise a solution of 4-chlorobenzene-sulphonyl chloride (3.90 g, 18.50 mmol) in methylene chloride (20 ml) and this solution was stirred for 24 h. The reaction mixture was then diluted with more methylene chloride (100 ml) and washed with water (2×75 ml). The organic layer was dried over $MgSO_4$, filtered and concentrated to give a crude product which was recrystallized from methanol to give n-eicosanyl-4-chlorobenzenesulphonate the product (5.10 g, 65%) m.p. 69°-70° C. max; 3000-2800, 1367, 1184, 1176, 963 cm$^{-1}$. m/z, 472 (M$^+$). Found C, 66.16%; H 9.75%; S, 6.74% Cl, 7.40% $C_{26}H_{45}O_3SCl$ requires C, 66.00%; H, 9.59%; S, 6.78%; Cl, 7.49%. $^1$Hnmr, 0.855 (t, J-6.6 Hz, 3H); 1.10-1.65 (m); 4.030 (t, J=6.4 Hz, 2H); 7.48-7.53 (m, 2H); 7.80-7.84 (m, 2H).

A stirred solution of 2-methylbenzoxazole (1.35 g, 10.10 mmol) and n-eicosanyl-4-chlorobenzenesulphonate (4.00 g, 8.50 mmol) was heated at 130°-135° C. for 24 h. After cooling, the solid formed was triturated with ether and washed 2 more times with ether. The product, 3-n-eicosanyl-2-methylbenzoxazolium-4-chlorobenzene-sulphonate, (4.20 g, 82%, m.p. 128°-132° C.) was allowed to air dry and used without further purification in the next step. v max; 3000-2800, 1593, 1582, 1219, 1207, 1086, 1030, 1007, 824, 754 cm$^{-1}$. $^1$Hnmr $\delta$, 0.87 (m, 3H) 1.10-1.95 (m); 3.20 (s, 3H); 4.62 (t, J-7.5 Hz, 2H); 7.12-7.72 (m, 8H). $^{13}$C nmr $\delta$, 168.1, 147.8, 144.5, 135.1, 129.6, 128.8, 127.9, 127.3, 114.1, 112.9, 47.9, 31.8, 29.6, 29.4, 29.3, 29.0, 28.1, 26.6, 22.6, 13.9. Found m/z (M+) 414.3764 $C_{28}H_{48}NO$ requires 414.3736.

A solution of 2-$\beta$-acetoniliodo)vinyl-1-benzo-xazolium-n-propyl iodide (0.448 g, 1.00 mmol) and 3-n-eicosanyl-2-methylbenzoxazolium-4-chlorobenzene-sulphonate (0.605 g, 1.00 mmol) in ethanol (15 ml) was heated to dissolve the salts and then triethylamine (0.40 ml) was added and the mixture heated at reflux for 1 h. The solution was then cooled and 15 ml of saturated KI solution was added. The solution was then diluted with water (150 ml) and extracted with methylene chrloride (150 ml). The methylene chloride layer was washed with water, dried over $MgSO_4$, filtered and concentrated to give a dark red gum which was crystallized from ethyl acetate to give brick red crystals of the desired product (0.42 g, 58%) m.p. 179°-180° C. v max: 3100-2800, 1564, 1506, 1211, 739 cm$^{-1}$. $^1$Hnmr $\delta$, 0.842 (t, J=7 Hz, 3H); 1.062-1.454 (m), 1.859-1.999 (m); 4.226 (t, J-7.4 Hz, 4H); 6.78 (d, J=13.2 Hz, 1H); 6.80 (d, J=13.2 Hz, 1H); 7.237-7.460 (m, 8H); 8.45 (t, J=13.2 Hz, 1H). Found C, 66.22%; H, 8.21%; N, 3.79% $C_{40}H_{59}O_2N_2$ requires C, 66.10%; H, 8.18%; N, 3.85%.

b. 3-n-pentyl-3'-n-octadecyloxacarbocyanine Iodide

A stirred solution of 2-methylbenzoxazole (10 g, 75 mmol) and n-pentyl iodide (14.85 g, 75 mmol) was heated at reflux for 18 h. After cooling, the yellow-brown solid was slurried in ether, filtered off and washed with ether. The resulting solid was air dried to give 3-n-pentyl-2-methylbenzoxazolium iodide (20.3 g, 82%).

A stirred mixture of 3-n-pentyl-2-methylbenzoxa-zolium (6.62 g, 20 mmol) and N,N'-diphenylformamidine (3.92 g, 20 mmol) in acetic anhydride (40 ml) was heated under reflux for 30 mins. The solution was then allowed to cool to room temperature, diluted with ether (200 ml) and refrigerated overnight. The crystalline solid, 2-($\beta$-acetonilido)vinyl-1-benzoxazolium n-pentyl iodide, which formed was filtered off washed with ether several times and air dried (5.88 g, 62%).

3-n-octadecyl-2-methylbenzoxazolium-4-chlorobenzene-sulphonate was prepared according to the procedure described by J. Sandermann, Liebigs Ann. Chem. 749, 183, 197 (1971).

The 3-n-pentyl-3-n-octadecyloxacarbocyanine iodide was prepared following essentially the same procedure used in Example 4a, with the following amounts of reagents: 2-($\beta$-Acetonilido)vinyl-1-benzoxazolium n-pentyl iodide (0.476 g, 1 mmol), 3-n-octadecyl-2-methylbenzoxazolium-4-chlorobenzene sulphonate (0.578 g, 1 mmol), triethylamine (0.40 ml) and ethanol (15 ml). The dark red crude product was recrystallized from ethyl acetate to give (0.45 g, 62%) m.p. 170°-173° C. v max: 3100-2800; 1565, 1507, 1209, 739 cm$^{-1}$. $^1$Hnmr $\delta$, 0.86-0.94 (m, 6H); 1.24-2.00 (m); 4.28 (t, J=7.1 Hz, 4H): 6.83 (d, J=13.4 Hz, 2H); 7.26-7.48 (m, 8H); 8.49 (dd, J=13 and 13.2 Hz, 1H). Found C, 66.39%; H, 8.13%: N, 3.79%; $C_{40}H_{59}N_2O_2I$ requires C, 66.10%; H, 8.18%; N, 3.85%.

c. 3-n-octyl-3'-n-octadecyloxacarbocyanine Iodide

A stirred solution of 2-methylbenzoxazole (10.0 g, 75 mmol) and n-octyl iodide (18.0 g, 75 mmol) was heated at reflux for 18 h. After cooling, the yellow-brown solid was slurried in ether, filtered and washed with ether. The resulting solid was air dried to give (20.5 g, 73%) of 3-n-octyl-2-methylbenzoxazolium iodide.

A stirred mixture 3-n-octyl-2-methylbenzoxazolium iodide (7.46 g, 0.02 mol) and N,N'-diphenylformamidine (3.92 g, 0.02 mol) in acetic anhydride (40 ml) was heated under reflux for 30 mins. The solution was then cooled and placed under high vacuum for 48 h. The crude product was then dissolved in methylene chloride, washed with water (2×50 ml), dried over magnesium sulphate, filtered and concentrated to give 2-($\beta$-acetonilido)vinyl-1-benzoxazolium n-octyl iodide as a crude product which was used without purification in the next reaction.

A solution of 2-($\beta$-Acetonilido)vinyl-1-benzoxazolium-n-octyl iodide (1.11 g) thus obtained and 3-n-octadecyl-2-methylbenzoxazolium 4-chlorobenzene sulphonate, prepared as described in Example 4b, (0.86 g, 1.50 mmol) in ethanol (20 ml) was heated to dissolve the salts and then triethylamine (0.60 ml) was added and the mixture heated at reflux for 1 h. The solution was cooled and 15 ml of saturated KI solution was added. The solution was then diluted with water (150 ml) and extracted with methylene chloride (150 ml). The methylene chloride layer was washed with water, dried over $MgSO_4$, filtered and concentrated and the dark red gum flash chromatographed on silica gel eluting with 5% methanol in $CH_2Cl_2$. The desired product was recrystallized from EtOAc to give (0.58 g, 50%) m.p. 166°–167° C. v max 1567, 1509, 1205, 739 cm$^{-1}$. $^1$Hnmr δ, 0.838–0.881 (m, 6H); 1.901–1.956 (m, 4H) 4.277 (t, J=6.5 Hz, 4H); 6.785 (d, J=13.1 Hz, 2H) 7.271–7.480 (m, 8H); 8.50 (t, J=13 Hz, 1H) m/z, 641 (M+). Found C 67.37%, H 8.51%, N 3.63%; $C_{43}H_{65}N_2O_2I$ requires C 67.17%; H 8.52%; N 3.64%.

d. 3-n-propyl-3-n-docosanyloxacarbocyanine Iodide

To a stirred solution of docosanol (6.0 g, 18.00 mmoL) and triethylamine (4 ml) in methylene chloride (80 ml) was added dropwise a solution of 4-chlorobenzene-nesulphonyl chloride (4.26 g, 20.00 mmoL) in methylene chloride (100 ml) and this solution was stirred for 24 h. The reaction mixture was then diluted with more methylene chloride (100 ml) and washed with water (2×75 ml). The organic layer was dried over $MgSO_4$, filtered and concentrated to give a crude product which was recrystallised from methanol to give n-docosanyl-4-chlorobenzenesulphonate (5.8 g, 65%) m.p. 74°–75° C. v max; 3000–2800, 1367, 1185, 1177, 963 cm$^{-1}$. $^1$Hnmr δ, 0.879 (m, 2H); 1.185–1.574 (m); 4.054 (t, J=6.6 Hz, 2H); 7.53 (d, J=8.8 Hz, 2H); 7.845 (d, J=8.8 Hz, 2H). m/z, 499 (M-H)$^+$. Found C, 67.13%; H, 10.13%; S, 6.36%; Cl, 7.26%; $C_{28}H_{49}O_3SCl$ requires C, 67.10%; H, 9.85; S, 6.40%; Cl, 7.07%.

A stirred solution of 2-methylbenzoxazole (0.665 g, 5 mmol and n-docosanyl-4-chlorobenzenesulphonate (2.5 g, 5 mmol) was heated at 130°–135° C. for 24 h. After cooling, the solid formed was triturated with ether and washed 2 more times with ether. The product 3-n-docosanyl-2-methylbenzoxazolium 4-chlorobenzene-sulphonate, (1.80 g, 56%) m.p. 115°–118° C. was allowed to air dry and used directly in the next reaction. v max; 3100–3000, 1595, 1582, 1220, 1198, 1086, 1032, 1008, 829, 756 cm$^{-1}$. $^1$Hnmr δ, 0.88 (m, 3H); 1.10–1.95 (m) 3.26 (s, 3H); 4.73 (t, J=7.4 Hz, 2H); 7.17–7.76 (m, 8H). $^{13}$Cnmr δ, 168.2, 147.8, 144.6, 135.0, 129.6, 128.7, 127.95, 127.3, 124.3, 114.1, 112.96, 47.9, 31.8, 29.6, 29.4, 29.3, 29.0, 28.1, 26.6, 22.6, 14.1, 14.0. Found m/z (M+) 442.4056 $C_{30}H_{52}NO$ requires 442.4049.

The 3-n-propyl-3'-n-docosanyloxacarbocyanine iodide was prepared following essentially the same procedure used in Example 4a, with the following amounts of reagents; 2-(β-Acetonilido)vinyl-1-benzoxazolium-n-propyl iodide (0.45 g, 1 mmol), 3-n-docosanyl-2-methyl-benzoxazolium 4-chlorobenzene-sulphonate (0.633 g, 1 mmol), triethylamine (0.40 ml) and ethanol (15 ml). The dark red crude product was crystallized from hot ethyl acetate to give brick red crystals of the product (0.45 g, 60%) m.p. 182°–184° C. v max: 3100–2800, 1565, 1507, 1209, 739 cm$^{-1}$. $^1$Hnmr δ, 0.879 (t, J=6.3 Hz, 3H); 1.105–2.049 (m); 4.264 (t, J=7.1 Hz, 4H); 6.85 (d, J=13 Hz, 1H); 6.86 (d, J=13.1 Hz, 1H); 7.258–7.485 (m, 8H); 8.488 (dd, J=13.0 and 13.2 Hz, 1H). Found C, 67.29%; H, 8.47%; N, 3.74%; $C_{42}H_{63}N_2O_2I$ requires C, 66.83%; H, 8.41%; N, 3.71%.

e. 3,6-bis (dimethylamino)-n-hexacosanyl acridinium Iodide

A solution of hexacosanol (250 mgs, 0.654 mmol), triethylamine (125 1, 0.900 mmol) and 4-chlorobenzenesulphonyl chloride (150 mgs, 0.711 mmol) in methylene chloride (30 ml) is stirred at room temperature for 120 h. The reaction mixture is then diluted with methylene chloride (20 ml) and washed with water (2×50 ml). The organic phase is dried over magnesium sulphate, filtered and concentrated to give a crude product. Flash column chromatography on silica gel (10:1 hexane:ethyl acetate) followed by recrystallization from methanol gives n-hexacosanyl-4-chlorobenzenesulphonate (80 mgs, 22%).

$V_{max}$; 3000–2800; 1367; 1185; 1177; 963; 831; 822 cm$^{-1}$. $^1$H nmr δ, 7.853 (d, J=8.7 Hz, 2H); 7.533 (d, J=8.6 Hz, 2H); 4.06 (t, J=6.5 Hz, 2H); 0.887 (t, J=6.3 Hz, 3H).

A solution of acridine orange (free base, 75% dye content) (71 mgs, 0.200 mmol) and n-hexacosanyl-4-chlorobenzenesulphonate (110 mgs, 0.200 mmol) in xylene (5 ml) is heated at reflux (oil bath temp 150° C.) for 24 h. The mixture is allowed to cool to room temperature and the xylene removed under high vacuum overnight. The solid residue is taken up in ethanol (10 ml) and saturated potassium iodide solution (10 ml) followed by water (10 ml) is added. The resulting solution is extracted with methylene chloride and the extract dried over magnesium sulphate, filtered and concentrated to give a crude product. Flash column chromatography (10% methanol in methylene chloride) of the crude material gave the product as a red crystalline solid (45 mgs, 30%). $V_{max}$; 3000–2800; 1640; 1601; 15037 1360; 1166 cm$^{-1}$. $^1$H nmr δ, 8.71 (s, 1H); 7.96 (d,J=9.3 Hz, 2H); 7.14 (dd, J=2.0 Hz and 9.0 Hz, 2H); 6.695 (s, 2H); 4.84 (t, J=7.9 Hz, 2H); 3.36 (s, 12H); 0,884 (t, J=7.0 Hz, 3H).

While the various aspects of the present invention have been described and exemplified above in terms of certain preferred embodiments, various other embodiments may be apparent to those skilled in the art. For example, the present invention may be used to advantage in the study of viruses. Currently, it is extremely difficult to track viruses within model systems to determine the location in vivo where viral replication or pooling takes place. Using the compounds of this invention, it is possible to incorporate reporter molecules into the lipids of membrane viruses, using both the fluorescent and radio-imaging procedures outlined hereinbelow. As an example, it is not known where the virus HIV-I (AIDS) replicates or resides within the living animal. Such viruses could be labeled with the Indium or Iodine (gamma-emitting) forms of the compounds of this invention and washed free of unbound radio-active compounds. The labeled virus would then be injected and the animal imaged using a gamma camera. If the viruses were also labeled with a fluorescent form of the compounds of this invention, then the gamma imaging could be used to identify which organ is the reservoir for the virus and the organ could be removed, disaggregated into single cell suspension and the cells containing the viruses could be identified on the basis of the fluorescence using flow cytometry or quantitative microscopy. This invention is, therefore, not limited to the embodiments specifically described and exemplified, but is capable of variation and modification without department from the scope of the appended claims.

What is claimed is:

1. A composition for binding a diagnostic agent to the surface membrane of a viable bioparticle capable of physiological function, said composition comprising a compound of the formula, R-B-R$_1$, wherein B represents a diagnostic agent selected from the group consisting of cyanine, acridine, pyridine, anthraquinone, coumarin, quinoline, xanthene, phenoxazine, phenothiazine and hexatriene dyes and and R and R$_1$ represent substituents independently selected from the group consisting of hydrogen, alkyl, alkenyl, alkynyl, alkaryl or aralkyl, the hydrocarbon chains of which are linear or branched, said substituents being unsubstituted or substituted with one or more non-polar functional groups, one of R or R$_1$ having at least 12 linear carbon atoms and the sum of the linear carbon atoms in R and R$_1$ totaling at least 23, said compound being sufficiently non-polar as to have a surface membrane retention coefficient of at least about 90 during a 24 hour period in saline containing up to 10 percent serum and the percent change in said coefficient during said period being less than 10 percent, and the compound solubility determination deviation of said compound being no more than 20 percent during two hours when dissolved in said binding medium; and a compatible binding medium in which said compound is dissolved, said medium being iso-osmotic for the bioparticle to which the compound is to be bound.

2. A composition as claimed in claim 1, wherein said medium has iso-osmotic properties at between 260 mOs and 340 mOs and is isotonic for the bioparticle to which the compound is to be bound.

3. A composition as claimed in claim 1, wherein said medium is selected from the group of a sugar, a sugar-alcohol, an amino acid, a Good's buffer or a combination thereof.

4. A composition for binding a diagnostic agent to the surface membrane of a viable bioparticle capable of physiological function, said composition comprising:

a) a compound having the formula:

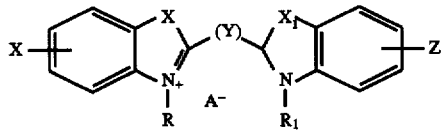

wherein R and $R_1$ are different and represent substituents independently selected from the group of hydrogen, alkyl, alkenyl, alkynyl, alkaryl or aralkyl, the hydrocarbon chains of which having from 1 to 30 carbon atoms, and being linear or branched, said substituents being unsubstituted or substituted with one or more non-polar functional groups, one of R or $R_1$ having at least 12 linear carbon atoms, and the sum of the linear carbon atoms in R and $R_1$ being at least 23;

X and $X_1$ may be the same or different and represent O, S, $C(CH_3)_2$ or Se;

Y represents a linking group selected from —CH=, —CH=CH—CH=, —CH=CH—CH=CH—CH=, or —CH=CH—CH=CH—CH=CH—CH=;

Z represents a substituent selected from the group H, alkyl, OH, $NH_2$, COOH, $CONH_2$, $SO_3H$, $SO_3NH_2$, CONH—alkyl, CON(alkyl)$_2$, NH-acyl, O-alkyl, NH-alkyl, N(alkyl)$_2$, SH, S-alkyl, $NO_2$ or halogen, the alkyl groups comprising said Z substituents having from 1 to 3 carbon atoms;

and A represents a biologically compatible anion; and b) a compatible binding medium in which said compound is dissolved, said medium being iso-osmotic for the bioparticle to which the compound is to be bound.

5. A composition for binding a diagnostic agent to the surface membrane of a viable bioparticle capable of physiological function, said composition comprising:

a) a compound having the formula:

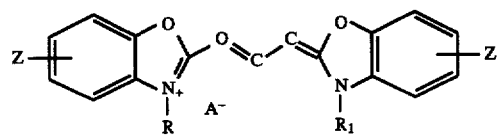

wherein R and $R_1$ are different and represent alkyl substituents, having from 1 to 30 carbon atoms, and being linear or branched, unsubstituted or substituted with halogen, one of R or $R_1$ having at least 12 linear carbon atoms and the sum of the linear atoms in R and $R_1$ being at least 23;

Z represents a substituent selected from the group H, or lower alkyl having from 1 to 3 carbon atoms; and A represents a biologically compatible anion; and a compatible binding medium in which said compound is dissolved, said medium being iso-osmotic for the bioparticle to which the compound is to be bound.

6. A composition as claimed in claim 5, wherein said compound is 3-n-Pentyl-3'-n-octadecyloxacarbocyanine Iodide.

7. A composition as claimed in claim 5, wherein said compound is 3-n-Octyl-3'-n-octadecyloxacarbocyanine Iodide.

8. A composition as claimed in claim 5, wherein said compound is 3-n-Propyl-3'-n-eicosanyloxacarbocyanine Iodide.

9. A composition as claimed in claim 5, wherein said compound is 3-n-Propyl-3'-n-docosanyloxacarbocyanine Iodide.

10. A composition for binding a diagnostic agent to the surface membrane of a viable bioparticle capable of physiological function, said composition comprising:

a) a compound of the formula:

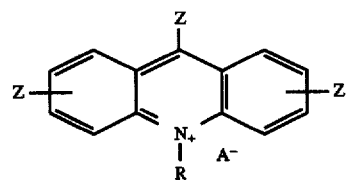

wherein R represents a substituent selected from the group of alkyl, alkenyl, alkynyl, alkaryl or aralkyl, the hydrocarbon chain of which is linear or branched, said substituent being unsubstituted or substituted with one or more non-polar functional groups, and having at least 23 linear carbon atoms;

Z represents a substituent selected from the group H, alkyl, OH, $NH_2$, COOH, $CONH_2$, $SO_3H$, $SO_2NH_2$, CONH-alkyl, CON-(alkyl)$_2$, NH-acyl, O-alkyl, NH-alkyl, N(alkyl)$_2$, SH, S-alkyl, $NO_2$ or halogen, the alkyl groups comprising said Z substituents having from 1 to 3 carbon atoms; and A represents a biologically compatible anion; and b) a compatible binding medium in which said compound is dissolved, said medium being iso-osmotic for the bioparticle to which the compound is to be bound.

11. A composition as claimed in claim 10, wherein said compound is 3,6-bis (dimethylamino)-10-n-hexacosanyl acridinium iodide.

12. A composition as claimed in claim 1, wherein said hydrocarbon substituent comprises a radioisotope.

13. A composition as claimed in claim 12, wherein said radioisotope is selected from the group of radioactive hydrogen, carbon, nitrogen, phosphorus, fluorine, chlorine, iodine, sulphur and selenium.

* * * * *

UNITED STATES PATENT AND TRADEMARK OFFICE
CERTIFICATE OF CORRECTION

PATENT NO. : 5,665,328 Page 1 of 1
DATED : September 9, 1997
INVENTOR(S) : Paul Karl Horan et al.

It is certified that error appears in the above-identified patent and that said Letters Patent is hereby corrected as shown below:

Column 31,
Table I, after the "PKH-8" line insert -- PKH-10   97.90   98.89   98.90   99.18   99.09   99.22   96.82   3.12 --;

Column 33,
Table II, enter the following figure before the "DiI-C5- (3)" figure --

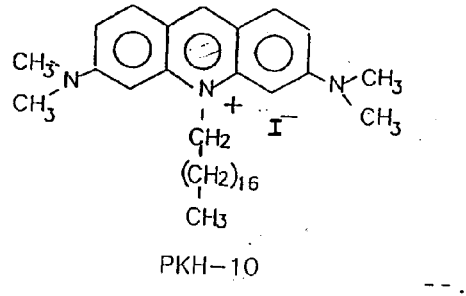

PKH-10

--.

Signed and Sealed this

Thirty-first Day of December, 2002

JAMES E. ROGAN
*Director of the United States Patent and Trademark Office*